US011167027B2

(12) United States Patent
Xu et al.

(10) Patent No.: US 11,167,027 B2
(45) **Date of Patent: *Nov. 9, 2021**

(54) MULTIVALENT FELINE VACCINE

(71) Applicant: Intervet Inc., Madison, NJ (US)

(72) Inventors: Zhichang Xu, Omaha, NE (US); Rhonda LaFleur, Omaha, NE (US); Ian Tarpey, St. Ives (GB)

(73) Assignee: Intervet Inc., Madison, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/760,160

(22) PCT Filed: Nov. 5, 2018

(86) PCT No.: PCT/EP2018/080106

§ 371 (c)(1),
(2) Date: Apr. 29, 2020

(87) PCT Pub. No.: WO2019/115090

PCT Pub. Date: Jun. 20, 2019

(65) Prior Publication Data

US 2020/0254088 A1 Aug. 13, 2020

Related U.S. Application Data

(60) Provisional application No. 62/599,401, filed on Dec. 15, 2017, provisional application No. 62/596,508, filed on Dec. 8, 2017, provisional application No. 62/582,050, filed on Nov. 6, 2017, provisional application No. 62/581,955, filed on Nov. 6, 2017.

(51) Int. Cl.

| | |
|---|---|
| ***A61K 39/295*** | (2006.01) |
| ***A61K 39/118*** | (2006.01) |
| ***A61K 39/12*** | (2006.01) |
| ***C12N 7/00*** | (2006.01) |
| *A61K 39/00* | (2006.01) |

(52) U.S. Cl.

CPC .......... *A61K 39/295* (2013.01); *A61K 39/118* (2013.01); *A61K 39/12* (2013.01); *C12N 7/00* (2013.01); *A61K 2039/53* (2013.01); *A61K 2039/552* (2013.01); *A61K 2039/70* (2013.01); *C12N 2770/36143* (2013.01)

(58) Field of Classification Search

None

See application file for complete search history.

(56) References Cited

U.S. PATENT DOCUMENTS

| | | | | |
|---|---|---|---|---|
| 7,449,323 B2 | | 11/2008 | Foley et al. | |
| 8,460,913 B2 | | 6/2013 | Kamrud et al. | |
| 8,685,412 B2 | * | 4/2014 | Huang | A61P 31/12 424/216.1 |
| 9,441,247 B2 | | 9/2016 | Rayner et al. | |
| 2008/0299149 A1 | * | 12/2008 | Wu | C12N 15/86 424/199.1 |
| 2013/0064839 A1 | | 3/2013 | Harris et al. | |
| 2015/0159143 A1 | * | 6/2015 | Dowdy | C07K 14/4705 435/7.1 |
| 2015/0299728 A1 | * | 10/2015 | Rayner | A61P 37/04 435/91.1 |
| 2020/0338186 A1 | | 10/2020 | Tarpey | |
| 2020/0345832 A1 | | 11/2020 | Tarpey | |

FOREIGN PATENT DOCUMENTS

| | | | |
|---|---|---|---|
| WO | 2001066568 A2 | | 9/2001 |
| WO | WO 2004/083390 | * | 9/2004 |
| WO | 2017109045 A1 | | 6/2017 |
| WO | WO 2017/109045 | * | 6/2017 |
| WO | 2019086646 A1 | | 5/2019 |

OTHER PUBLICATIONS

Alignment of SEQ ID 2 with Geneseq db access No. BEB26323 in WO 2017109045 Aug. 2017 by Shehu et al.*
Alignment of SEQ ID 4 with Geneseq db access No. BEB26324 in WO 2017109045 Jun. 2017 by Shehu et al.*
Alignment of SEQ ID No. 6 with Geneseq db access AZY06317 in US2012183569 on Sep. 2012 by Poulet et al.*
Alignment with SEQ 10 with Geneseq db access AAP70320 in EP237686 on Sep. 1987 by Tordo et al.*
Carroll et al. (Vaccine. 2011; 29: 931-940).*
Arjona, Alvaro et al., Seroepidemiological Survey of Infection by Feline Leukemia Virus and Immunodeficiency Virus in Madrid and Correlation with Some Clinical Aspects, Journal of Clinical Microbiology, 2000, 3448-3449, 38.
Atkins, GJ et al, Therapeutic and prophylactic applications of alphavirus vectors, Expert Reviews in Molecular Medicine, 2008, e33, 1-18, 10(1).
Braley, JO, FeLV and FIV: Survey Shows Prevalence in the United States and Europe, Feline Practice—Infectious Disease, 1994, 25-29, 22.
Bredenbeek, Peter J. et al., Sindbis Virus Expression Vectors: Packaging of RNA Replicons by Using Defective Helper RNAs, Journal of Virology, 1993, 6439-6446, 67(11).
De Noronha, F. et al., Influence of Antisera To Oncornavirus Glycoprotein (gp71) on Infections of Cats with Feline Leukemia Virus, Virology, 1978, 617-621, 85.
Flynn, J. Norman et al., Longitudinal Analysis of Feline Leukemia Virus-Specific Cytotoxic T Lymphocytes: Correlation with Recovery from Infection, Journal of Virology, 2002, 2306-2315, 76(5).
Grosenbaugh, DA et al, Comparison of the Safety and Efficacy of a Recombinant Feline Leukemia Virus (FeLV) Vaccine Delivered Transdermally and an Inactivated FeLV Vaccine Delivered Subcutaneously, Veterinary Therapeutics, Veterinary Learning Systems, 2004, 258-262, 5(4).
Hardy, Jr., William D. et al., Ten-year study comparing enzyme-linked immunosorbent assay with the immunofluorescent antibody test for detection of feline leukemia virus infection in cats, JAVMA, 1991, 1365-1373, 199(10).

(Continued)

*Primary Examiner* — Shanon A. Foley
(74) *Attorney, Agent, or Firm* — Michael D. Davis

(57) ABSTRACT

The present invention provides new multivalent vaccines for felines. The present invention also provides methods of making and using the multivalent vaccines alone or in combinations with other protective agents.

20 Claims, No Drawings

Specification includes a Sequence Listing.

(56) References Cited

OTHER PUBLICATIONS

Hines, David L. et al., Evaluation of efficacy and safety of an inactivated virus vaccine against feline leukemia virus infection, J. Am. Vet. Med. Assoc., 1991, 1428-1430, 199.
Hoover, Edward A. et al., Feline leukemia virus infection and diseases, J. Am. Vet. Med. Assoc., 1991, 1287-1297, 199.
Hosie, M.J. et al., Prevalence of feline leukaemia virus and antibodies to feline immunodeficiency virus in cats in the United Kingdom, Veterinary Records, 1989, 293-297, 128.
International Search Report for PCT/EP2018/080106 dated Mar. 15, 2019, 18 pages.
Kamrud, K.I. et al., Development and characterization of promoterless helper RNAs for the production of alphavirus replicon particle, Journal of General Virology, 2010, 1723-1727, 91(Pt 7).
Kass, P et al, Epidemiologic evidence for a causal relation between vaccination and fibrosarcoma tumorigenesis in cats, Journal of the American Veterinary Medical Association, 1993, 396-405, 203(3).
Konopka, Jennifer L. et al., Acute Infection with Venezuelan Equine Encephalitis Virus Replicon Particles Catalyzes a Systemic Antiviral State and Protects from Lethal Virus Challenge, Journal of Virology, 2009, 12432-12442, 83(29).
Levy, Julie et al., 2008 American Association of Feline Practitioners' feline retrovirus management guidelines, Journal of Feline Medicine and Surgery, 2008, 300-316, 10.
Liljestrom, P. et al., A new generation of animal cell expression vectors based on the semliki forest virus replicon, Biotechnology, 1991, pp. 1356-1361, 9.
Liu, Chunguo et al., Complete Genome Sequence of Feline Panleukopenia Virus Strain HRB-CS1, Isolated from a Domestic Cat in Northeastern China, Genome Announcements, 2015, 1, 3(2):e01556-14.
Ljungberg, K et al, Self-replicating alphavirus RNA vaccines, Expert Review of Vaccines, 2015, 177-194, 14(2).
Lucchese, G et al, How a single amino acid change may alter the immunological information of a peptide, Frontiers in Bioscience: Elite Edition, 2012, 1843-1852, vol. 4, No. 5.
Malik, R. et al., Prevalences of feline leukaemia virus and feline immunodeficiency virus infections in cats in Sydney, Australian Veterinary Journal, 1997, 323-327, 75.
Mathes L.E. et al., Abrogation of lymphocyte blastogenesis by a feline leukaemia virus protein, Nature, 1978, 687-689, 274.
Nunberg, J.H. et al., Method to map antigenic determinants recognized by monoclonal antibodies: Localization of a determinant of virus neutralization on the feline leukemia virus envelope protein gp70, Proc. Natl. Acad. Sci. USA, 1984, 3675-3679, 81.
Pacitti, A.M. et al., Transmission of feline leukaemia virus in the milk of a non-viraemic cat, The Veterinary Record, 1986, 381-384, 118.
Patel, M et al, Comparative Efficacy of Feline Leukemia Virus (FeLV) Inactivated Whole-Virus Vaccine and Canarypox Virus-Vectored Vaccine during Virulent FeLV Challenge and Immunosuppression, Abstract, Clinical and Vaccine Immunology, 2015, 798-805, 22(7).
Pedersen, Niels C., Immunogenicity and Efficacy of a Commercial Feline Leukemia Virus Vaccine, J. Vet. Intern. Med., 1993, 34-39, 7.
Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.
Radford, Alan D. et al., Feline calicivirus, Vet. Res., 2007, 319-335, 38(2).
Rayner, Jo et al., Alphavirus vectors and vaccination, Reviews in Medical Virology, 2002, pp. 279-296, 12.
Reed, DS et al, Combined Alphavirus Replicon Particle Vaccine Induces Durable and Cross-Protective Immune Responses against Equine Encephalitis Viruses, Journal of Virology, 2014, 12077-12086, vol. 88, No. 20.
Rojko, Jennifer L. et al., Pathogenesis of infection by the feline leukemia virus, J Am Vet Med Assoc, 1991, 1305-1310, 199.
Scherk, M.A., et al., 2013 AAFP Feline Vaccination Advisory Panel Report, Journal of Feline Medicine and Surgery, 2013, pp. 785-808, 15.
Scott, Fred W et al., Long-term immunity in cats vaccinated with an inactivated trivalent vaccine, Am. J. Vet. Res., 1999, 652-658, 60.
Segundo, Fayna Diaz-San et al., Venezuelan Equine Encephalitis Replicon Particles Can Induce Rapid Protection against Foot-and-Mouth Disease Virus, Journal of Virology, 2013, 5447-5460, 87(10).
Sosnovtsev, Stanislav V. et al., Identification and Genomic Mapping of the ORF3 and VPg Proteins in Feline Calicivirus Virions, Virology, 2000, 193-203, 277.
Sparkes, A.H., Feline leukaentia virus: a revie-w of immunity and vaccination, Journal of Small Animal Practice, 1997, 187-194, 38.
Stuke, K et al, Efficacy of an inactivated FeLV vaccine compared to a recombinant FeLV vaccine in minimum age cats following virulent FeLV challenge, Vaccine, 2014, 2599-2603, 32(22).
Thomsen, Darrell R. et al., Expression of feline leukaemia virus gp85 and gag proteins and assembly into virus-like particles using the baculovirus expression vector system, Journal of General Virology, 1992, 1819-1824, 73.
Torres, Andrea N. et al., Feline leukemia virus immunity induced by whole inactivated virus vaccination, Veterinary Immunology and Immunopathology, 2010, 122-131, 134.
Uematus, Y et al, Lack of Interference with Immunogenicity of a Chimeric Alphavirus Replicon Particle-Based Influenza Vaccine by Preexisting Antivector Immunity, Clinical and Vaccine Immunology, 2012, 991-998, vol. 19, No. 7.
Vander Veen, RL et al, Alphavirus replicon vaccines, Animal Health Research Reviews, 2012, 1-9, vol. 13, No. 1.

* cited by examiner

SEQUENCE LISTING

<160> NUMBER OF SEQ ID NOS: 16

<210> SEQ ID NO 1
<211> LENGTH: 1638
<212> TYPE: DNA
<213> ORGANISM: Artificial Sequence
<220> FEATURE:
<223> OTHER INFORMATION: codon optimized for feline

<400> SEQUENCE: 1

```
atggctgacg acggatctgt gaccacccca gaacaaggaa caatggtcgg aggagtgatt      60

gccgaaccca gcgctcagat gtcaactgcg gcggacatgg cctccggaaa gtcggtggac     120

tccgagtggg aagccttctt ctcgttccac acgtccgtga actggagcac ctccgaaacc     180

caaggaaaga tcctcttcaa gcagtccctg ggtcccctgc tgaacccgta cctggagcac     240

atcagcaagc tgtacgtcgc ttggagcggg tcgatcgaag tgcgatttc catctcggga     300

agcggcgtgt tcggtggtaa actggccgcc atcgtcgtgc cgcctggtgt cgaccctgtc     360

cagtcaacct ccatgctgca gtacccgcac gtcctgttcg acgcaagaca agtggagcca     420

gtgatcttct ccatcccgga cctccgcaac agcctgtatc acttgatgtc cgataccgat     480

accacttccc tcgtgatcat ggtgtacaac gatctgatca acccgtacgc caatgactcc     540

aacagctcgg gttgcatcgt gaccgtcgaa acgaagcctg gcatcgattt caagtttcat     600

ctgctgaaac cgcccggatc catgcttact cacgggtcca tcccttccga tctgatcccc     660

aagagctcct ccctgtggat tgggaaccgc cactggaccg atattaccga tttcgtgatt     720

cggcctttcg tgttccaagc caaccggcac ttcgacttca accaggagac tgccggctgg     780
```

-continued

```
tcaactccac ggttccgccc attggccgtg actgtgtcgc agtcaaaggg agccaagctc    840

gggaacggca tcgccaccga ctacattgtg cctggaatcc ccgacggatg gcctgatact    900

accatcccca ccaagctgac ccctaccgga gattacgcca tcacctcctc cgacggcaat    960

gatattgaaa ccaagctgga atacgagaac gcggacgtga ttaagaacaa caccaacttc   1020

cgctccatgt atatctgcgg aagcctccag agggcttggg gcgacaagaa gatcagcaac   1080

accgggttca tcactaccgg agtgatttct gacaactcca tcagcccttc gaacacaatt   1140

gaccagtcca agatcgtggt gtaccaggac aaccatgtca attcggaggt ccagactagc   1200

gacatcactc ttgccatcct gggctacacc ggaattggag aagaggccat aggcgccaac   1260

cgggactccg tcgtgagaat ttccgtgctt ccggaaactg gagcaagggg cggaaatcac   1320

cccatcttct acaaaaattc catgaagctg ggctacgtga tctcctccat tgacgtgttc   1380

aactcccaaa tcctccacac ctcgcgccag ctgtcactga acaactactt gttgcccccct  1440

gactccttcg cggtgtaccg gattattgac agcaacggat catggttcga cattgggatt   1500

gacagcgatg ggttttcatt cgtgggcgtg tcgtcatttc caaagctgga gtttccgctg   1560

tccgcctcat acatgggcat ccagctcgca aagatccggc tggcgtccaa catccggtca   1620

tccatgacta agctgtga                                                 1638
```

<210> SEQ ID NO 2
<211> LENGTH: 545
<212> TYPE: PRT
<213> ORGANISM: Feline calicivirus

<400> SEQUENCE: 2

```
Met Ala Asp Asp Gly Ser Val Thr Thr Pro Glu Gln Gly Thr Met Val
1               5                   10                  15

Gly Gly Val Ile Ala Glu Pro Ser Ala Gln Met Ser Thr Ala Ala Asp
            20                  25                  30

Met Ala Ser Gly Lys Ser Val Asp Ser Glu Trp Glu Ala Phe Phe Ser
        35                  40                  45

Phe His Thr Ser Val Asn Trp Ser Thr Ser Glu Thr Gln Gly Lys Ile
    50                  55                  60

Leu Phe Lys Gln Ser Leu Gly Pro Leu Leu Asn Pro Tyr Leu Glu His
65                  70                  75                  80

Ile Ser Lys Leu Tyr Val Ala Trp Ser Gly Ser Ile Glu Val Arg Phe
                85                  90                  95

Ser Ile Ser Gly Ser Gly Val Phe Gly Gly Lys Leu Ala Ala Ile Val
            100                 105                 110

Val Pro Pro Gly Val Asp Pro Val Gln Ser Thr Ser Met Leu Gln Tyr
        115                 120                 125

Pro His Val Leu Phe Asp Ala Arg Gln Val Glu Pro Val Ile Phe Ser
    130                 135                 140

Ile Pro Asp Leu Arg Asn Ser Leu Tyr His Leu Met Ser Asp Thr Asp
145                 150                 155                 160

Thr Thr Ser Leu Val Ile Met Val Tyr Asn Asp Leu Ile Asn Pro Tyr
                165                 170                 175

Ala Asn Asp Ser Asn Ser Ser Gly Cys Ile Val Thr Val Glu Thr Lys
            180                 185                 190

Pro Gly Ile Asp Phe Lys Phe His Leu Leu Lys Pro Pro Gly Ser Met
        195                 200                 205

Leu Thr His Gly Ser Ile Pro Ser Asp Leu Ile Pro Lys Ser Ser Ser
```

-continued

```
    210                 215                 220

Leu Trp Ile Gly Asn Arg His Trp Thr Asp Ile Thr Asp Phe Val Ile
225                 230                 235                 240

Arg Pro Phe Val Phe Gln Ala Asn Arg His Phe Asp Phe Asn Gln Glu
                245                 250                 255

Thr Ala Gly Trp Ser Thr Pro Arg Phe Arg Pro Leu Ala Val Thr Val
            260                 265                 270

Ser Gln Ser Lys Gly Ala Lys Leu Gly Asn Gly Ile Ala Thr Asp Tyr
        275                 280                 285

Ile Val Pro Gly Ile Pro Asp Gly Trp Pro Asp Thr Thr Ile Pro Thr
    290                 295                 300

Lys Leu Thr Pro Thr Gly Asp Tyr Ala Ile Thr Ser Ser Asp Gly Asn
305                 310                 315                 320

Asp Ile Glu Thr Lys Leu Glu Tyr Glu Asn Ala Asp Val Ile Lys Asn
                325                 330                 335

Asn Thr Asn Phe Arg Ser Met Tyr Ile Cys Gly Ser Leu Gln Arg Ala
            340                 345                 350

Trp Gly Asp Lys Lys Ile Ser Asn Thr Gly Phe Ile Thr Thr Gly Val
        355                 360                 365

Ile Ser Asp Asn Ser Ile Ser Pro Ser Asn Thr Ile Asp Gln Ser Lys
    370                 375                 380

Ile Val Val Tyr Gln Asp Asn His Val Asn Ser Glu Val Gln Thr Ser
385                 390                 395                 400

Asp Ile Thr Leu Ala Ile Leu Gly Tyr Thr Gly Ile Gly Glu Glu Ala
                405                 410                 415

Ile Gly Ala Asn Arg Asp Ser Val Val Arg Ile Ser Val Leu Pro Glu
            420                 425                 430

Thr Gly Ala Arg Gly Gly Asn His Pro Ile Phe Tyr Lys Asn Ser Met
        435                 440                 445

Lys Leu Gly Tyr Val Ile Ser Ser Ile Asp Val Phe Asn Ser Gln Ile
    450                 455                 460

Leu His Thr Ser Arg Gln Leu Ser Leu Asn Asn Tyr Leu Leu Pro Pro
465                 470                 475                 480

Asp Ser Phe Ala Val Tyr Arg Ile Ile Asp Ser Asn Gly Ser Trp Phe
                485                 490                 495

Asp Ile Gly Ile Asp Ser Asp Gly Phe Ser Phe Val Gly Val Ser Ser
            500                 505                 510

Phe Pro Lys Leu Glu Phe Pro Leu Ser Ala Ser Tyr Met Gly Ile Gln
        515                 520                 525

Leu Ala Lys Ile Arg Leu Ala Ser Asn Ile Arg Ser Ser Met Thr Lys
    530                 535                 540

Leu
545


<210> SEQ ID NO 3
<211> LENGTH: 1629
<212> TYPE: DNA
<213> ORGANISM: Artificial Sequence
<220> FEATURE:
<223> OTHER INFORMATION: codon optimized for feline

<400> SEQUENCE: 3

atgactgccc cggaacaagg aacgatggtc ggaggagtga ttgcagaacc gtcagcacag      60

atgtccaccg ctgccgacat ggccactgga aagagcgtgg actccgaatg ggaagccttc     120
```

-continued

```
ttctccttcc acacttcggt caactggtcg actagcgaaa cccaggggaa gattttgttc    180

aagcaatccc tcggccctct gctgaacccc tacctggagc atctggccaa gctgtacgtg    240

gcatggtcgg gcagcatcga agtgcgcttt agcatttccg gctccggagt gttcgggggga    300

aagcttgctg ccattgtcgt gccgccagga gtggacccgg tgcagtccac ttctatgctc    360

caatacccgc atgtcctgtt cgacgccaga caggtggagc ctgtgatctt ttgcctgccg    420

gatctcaggt ccaccctgta tcacctcatg tccgacaccg acaccacctc gctcgtgatc    480

atggtgtaca acgacctgat caacccctac gctaacgacg ccaacagctc aggttgcatt    540

gtgactgtcg aaaccaagcc aggccctgac ttcaagtttc atttgctgaa gccgcccggt    600

tccatgctga cccacggctc gatcccatcc gacctgatcc ccaagacgag ctccctgtgg    660

atcggaaacc gctactggtc cgatattacc gacttcgtga tcagaccatt cgtgttccaa    720

gccaaccgcc atttcgactt caaccaggaa accgcaggat ggtcgacccc tcgattccgc    780

ccgatttcag tgaccatcac cgaacagaac ggcgcgaagc tgggaattgg cgtggcgacc    840

gactacatcg tgccgggaat cccggatgga tggcctgata cgaccattcc cggggagctg    900

atccctgccg gggactacgc catcaccaac ggtactggaa acgacatcac cactgccacc    960

ggttacgaca ccgccgacat cataaagaac aacaccaact tcagaggaat gtacatttgc   1020

ggctccctgc aacgcgcttg gggtgacaaa aagatctcga acactgcctt catcacaaca   1080

gcgactctgg acggcgataa caacaacaag atcaatcctt gtaataccat cgaccagtcc   1140

aaaatcgtgg tgttccagga taaccacgtg ggaaagaagg cgcagacctc cgacgacact   1200

ctggcgctgc ttggctacac cgggatcggc gagcaggcca ttggaagcga tcgggatcgg   1260

gtcgtgcgga tctccaccct ccccgagact ggagcaaggg gaggcaacca ccccatcttt   1320

tacaaaaaca gcattaagct cggatacgtc atccgctcca tcgatgtgtt caactctcaa   1380

atcctgcaca cttcgcggca gctgtccctg aaccactacc tcttgccgcc cgactccttc   1440

gccgtctacc ggatcattga ttcgaacggg agctggttcg acatcggcat tgatagcgat   1500

ggcttctcgt ttgtgggcgt gtcgggcttc gggaagctgg agttcccact gagcgcctca   1560

tacatgggta tccagctggc caagatcagg ctggcctcca acatccgctc acctatgact   1620

aagctgtga                                                           1629


<210> SEQ ID NO 4
<211> LENGTH: 542
<212> TYPE: PRT
<213> ORGANISM: Feline calicivirus

<400> SEQUENCE: 4

Met Thr Ala Pro Glu Gln Gly Thr Met Val Gly Gly Val Ile Ala Glu
1               5                   10                  15

Pro Ser Ala Gln Met Ser Thr Ala Ala Asp Met Ala Thr Gly Lys Ser
            20                  25                  30

Val Asp Ser Glu Trp Glu Ala Phe Phe Ser Phe His Thr Ser Val Asn
        35                  40                  45

Trp Ser Thr Ser Glu Thr Gln Gly Lys Ile Leu Phe Lys Gln Ser Leu
    50                  55                  60

Gly Pro Leu Leu Asn Pro Tyr Leu Glu His Leu Ala Lys Leu Tyr Val
65                  70                  75                  80

Ala Trp Ser Gly Ser Ile Glu Val Arg Phe Ser Ile Ser Gly Ser Gly
                85                  90                  95

Val Phe Gly Gly Lys Leu Ala Ala Ile Val Val Pro Pro Gly Val Asp
```

-continued

```
            100                 105                 110

Pro Val Gln Ser Thr Ser Met Leu Gln Tyr Pro His Val Leu Phe Asp
        115                 120                 125

Ala Arg Gln Val Glu Pro Val Ile Phe Cys Leu Pro Asp Leu Arg Ser
    130                 135                 140

Thr Leu Tyr His Leu Met Ser Asp Thr Asp Thr Thr Ser Leu Val Ile
145                 150                 155                 160

Met Val Tyr Asn Asp Leu Ile Asn Pro Tyr Ala Asn Asp Ala Asn Ser
                165                 170                 175

Ser Gly Cys Ile Val Thr Val Glu Thr Lys Pro Gly Pro Asp Phe Lys
            180                 185                 190

Phe His Leu Leu Lys Pro Pro Gly Ser Met Leu Thr His Gly Ser Ile
        195                 200                 205

Pro Ser Asp Leu Ile Pro Lys Thr Ser Ser Leu Trp Ile Gly Asn Arg
    210                 215                 220

Tyr Trp Ser Asp Ile Thr Asp Phe Val Ile Arg Pro Phe Val Phe Gln
225                 230                 235                 240

Ala Asn Arg His Phe Asp Phe Asn Gln Glu Thr Ala Gly Trp Ser Thr
                245                 250                 255

Pro Arg Phe Arg Pro Ile Ser Val Thr Ile Thr Glu Gln Asn Gly Ala
            260                 265                 270

Lys Leu Gly Ile Gly Val Ala Thr Asp Tyr Ile Val Pro Gly Ile Pro
        275                 280                 285

Asp Gly Trp Pro Asp Thr Thr Ile Pro Gly Glu Leu Ile Pro Ala Gly
    290                 295                 300

Asp Tyr Ala Ile Thr Asn Gly Thr Gly Asn Asp Ile Thr Thr Ala Thr
305                 310                 315                 320

Gly Tyr Asp Thr Ala Asp Ile Ile Lys Asn Asn Thr Asn Phe Arg Gly
                325                 330                 335

Met Tyr Ile Cys Gly Ser Leu Gln Arg Ala Trp Gly Asp Lys Lys Ile
            340                 345                 350

Ser Asn Thr Ala Phe Ile Thr Thr Ala Thr Leu Asp Gly Asp Asn Asn
        355                 360                 365

Asn Lys Ile Asn Pro Cys Asn Thr Ile Asp Gln Ser Lys Ile Val Val
    370                 375                 380

Phe Gln Asp Asn His Val Gly Lys Lys Ala Gln Thr Ser Asp Asp Thr
385                 390                 395                 400

Leu Ala Leu Leu Gly Tyr Thr Gly Ile Gly Glu Gln Ala Ile Gly Ser
                405                 410                 415

Asp Arg Asp Arg Val Val Arg Ile Ser Thr Leu Pro Glu Thr Gly Ala
            420                 425                 430

Arg Gly Gly Asn His Pro Ile Phe Tyr Lys Asn Ser Ile Lys Leu Gly
        435                 440                 445

Tyr Val Ile Arg Ser Ile Asp Val Phe Asn Ser Gln Ile Leu His Thr
    450                 455                 460

Ser Arg Gln Leu Ser Leu Asn His Tyr Leu Leu Pro Pro Asp Ser Phe
465                 470                 475                 480

Ala Val Tyr Arg Ile Ile Asp Ser Asn Gly Ser Trp Phe Asp Ile Gly
                485                 490                 495

Ile Asp Ser Asp Gly Phe Ser Phe Val Gly Val Ser Gly Phe Gly Lys
            500                 505                 510

Leu Glu Phe Pro Leu Ser Ala Ser Tyr Met Gly Ile Gln Leu Ala Lys
        515                 520                 525
```

-continued

Ile Arg Leu Ala Ser Asn Ile Arg Ser Pro Met Thr Lys Leu
530 535 540

<210> SEQ ID NO 5
<211> LENGTH: 1929
<212> TYPE: DNA
<213> ORGANISM: Artificial Sequence
<220> FEATURE:
<223> OTHER INFORMATION: codon optimized for feline

<400> SEQUENCE: 5
atggagtcac caacacaccc taaaccttct aaagacaaaa ccctctcgtg gaatctcgcc 60
ttccttgtgg gcatcctgtt cacaatcgac atcggcatgg ccaacccttc gccgcatcag 120
atctacaatg tgacatgggt cattactaat gtgcagacaa acacccaggc aaatgctact 180
tctatgcttg gtactctgac tgatgcttat ccaaccctgc acgtcgacct ttgcgatctc 240
gtcggtgaca catgggagcc catcgtgctg aatccaacta atgtcaaaca tggtgccagg 300
tattcttcta gcaaatacgg gtgtaagacc actgatcgga agaaacagca acaaacctac 360
ccattctacg tgtgcccggg tcacgcaccg tccctgggtc cgaagggaac acattgtggg 420
ggagcccaag acggtttttg cgctgcttgg ggttgtgaaa caaccggaga agcctggtgg 480
aagcctacct catcttggga ctacattact gtgaaaagag gctctagcca ggataacagc 540
tgcgaaggaa agtgtaatcc cctggtgctt caattcaccc agaaaggccg gcaggcatca 600
tgggatggac cgaaaatgtg gggacttaga ctctatcgca ccggatacga ccccatcgct 660
ctgtttactg tgtcacgcca agtctccacc attactccgc cacaggccat ggggccgaat 720
ctggtcctcc ccgatcagaa gccaccctca cggcaaagtc aaaccggctc aaaagtggcc 780
acccaacggc cccagacaaa tgagtccgca cctaggtcag tggcacctac aacaatgggt 840
ccaaagcgga tcggaaccgg agacaggctc attaacctcg tgcaagggac ttatctggcc 900
cttaacgcta ctgaccccaa caagaccaag gattgctggc tctgccttgt gagcagacct 960
ccttactatg aggggatcgc cattctcgga aactactcaa atcagaccaa ccccccctccg 1020 tcgtgtctga gcaccccccca gcacaagctt actatttcag aagtcagtgg acagggaatg 1080
tgcatcggaa ccgtgccaaa gactcatcaa gccctttgca acaaaactca acaagggcac 1140
actggagctc attatctcgc cgcacctaac gggacctact gggcttgcaa tactggattg 1200
accccgtgta tctctatggc cgtgctgaat tggacttccg acttctgcgt gcttattgag 1260
ctttggccta gagtgacata ccatcagcct gagtacgtct atacccattt cgccaaggca 1320
gtcagattcc ggcgggagcc tatctccctg actgtggcct tgatgctcgg tggactgaca 1380
gtgggaggaa ttgcagctgg agtcggaact ggaaccaagg ccctgctcga aactgctcag 1440
ttccggcagc tgcagatggc catgcacact gacatccagg ctctggagga atcaatttca 1500
gcccttgaga aaagcttgac ctcgctgtct gaagtggtcc tccaaaacag gcgcggtttg 1560
gacatcctgt tccttcaaga gggtggtctg tgcgccgctc tcaaggagga atgctgtttc 1620
tacgctgacc ataccgggct ggtgcgcgat aacatggcaa agctgcggga acgcttgaaa 1680
cagaggcagc aactgttcga ctctcagcag ggatggttcg agggctggtt taacaagagc 1740
ccatggttta ccactctgat ctcttcaatc atgggtccac tgctcatcct gcttctgatt 1800
cttctcttcg gaccgtgtat tctcaacagg ctggtgcagt ttgtcaagga cagaatctcg 1860
gtggtccagg ccctgattct tactcagcag tatcagcaga ttaagcagta cgaccccgat 1920
cggccttga 1929

<210> SEQ ID NO 6
<211> LENGTH: 642
<212> TYPE: PRT
<213> ORGANISM: Feline leukemia virus

<400> SEQUENCE: 6

Met Glu Ser Pro Thr His Pro Lys Pro Ser Lys Asp Lys Thr Leu Ser
1 5 10 15

Trp Asn Leu Ala Phe Leu Val Gly Ile Leu Phe Thr Ile Asp Ile Gly
20 25 30

Met Ala Asn Pro Ser Pro His Gln Ile Tyr Asn Val Thr Trp Val Ile
35 40 45

Thr Asn Val Gln Thr Asn Thr Gln Ala Asn Ala Thr Ser Met Leu Gly
50 55 60

Thr Leu Thr Asp Ala Tyr Pro Thr Leu His Val Asp Leu Cys Asp Leu
65 70 75 80

Val Gly Asp Thr Trp Glu Pro Ile Val Leu Asn Pro Thr Asn Val Lys
85 90 95

His Gly Ala Arg Tyr Ser Ser Ser Lys Tyr Gly Cys Lys Thr Thr Asp
100 105 110

Arg Lys Lys Gln Gln Gln Thr Tyr Pro Phe Tyr Val Cys Pro Gly His
115 120 125

Ala Pro Ser Leu Gly Pro Lys Gly Thr His Cys Gly Gly Ala Gln Asp
130 135 140

Gly Phe Cys Ala Ala Trp Gly Cys Glu Thr Thr Gly Glu Ala Trp Trp
145 150 155 160

Lys Pro Thr Ser Ser Trp Asp Tyr Ile Thr Val Lys Arg Gly Ser Ser
165 170 175

Gln Asp Asn Ser Cys Glu Gly Lys Cys Asn Pro Leu Val Leu Gln Phe
180 185 190

Thr Gln Lys Gly Arg Gln Ala Ser Trp Asp Gly Pro Lys Met Trp Gly
195 200 205

Leu Arg Leu Tyr Arg Thr Gly Tyr Asp Pro Ile Ala Leu Phe Thr Val
210 215 220

Ser Arg Gln Val Ser Thr Ile Thr Pro Pro Gln Ala Met Gly Pro Asn
225 230 235 240

Leu Val Leu Pro Asp Gln Lys Pro Pro Ser Arg Gln Ser Gln Thr Gly
245 250 255

Ser Lys Val Ala Thr Gln Arg Pro Gln Thr Asn Glu Ser Ala Pro Arg
260 265 270

Ser Val Ala Pro Thr Thr Met Gly Pro Lys Arg Ile Gly Thr Gly Asp
275 280 285

Arg Leu Ile Asn Leu Val Gln Gly Thr Tyr Leu Ala Leu Asn Ala Thr
290 295 300

Asp Pro Asn Lys Thr Lys Asp Cys Trp Leu Cys Leu Val Ser Arg Pro
305 310 315 320

Pro Tyr Tyr Glu Gly Ile Ala Ile Leu Gly Asn Tyr Ser Asn Gln Thr
325 330 335

Asn Pro Pro Pro Ser Cys Leu Ser Thr Pro Gln His Lys Leu Thr Ile
340 345 350

Ser Glu Val Ser Gly Gln Gly Met Cys Ile Gly Thr Val Pro Lys Thr
355 360 365

His Gln Ala Leu Cys Asn Lys Thr Gln Gln Gly His Thr Gly Ala His

```
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro


<210> SEQ ID NO 7
<211> LENGTH: 1233
<212> TYPE: DNA
<213> ORGANISM: Artificial Sequence
<220> FEATURE:
<223> OTHER INFORMATION: codon optimized for feline

<400> SEQUENCE: 7

aatcctagtc cacaccaaat atataatgta acttgggtaa taaccaatgt acaaactaac     60

acccaagcta acgccacctc tatgttagga accttaaccg atgcctaccc taccctacat    120

gttgacttat gtgacctagt gggagacacc tgggaaccta tagtcctaaa cccaaccaat    180

gtaaaacacg gggcacgtta ctcctcctca aaatatggat gtaaaactac agatagaaaa    240

aaacagcaac agacataccc cttttacgtc tgccccggac atgccccctc gttggggcca    300

aagggaacac attgtggagg ggcacaagat gggttttgtg ccgcatgggg atgtgagacc    360

accggagaag cttggtggaa gcccacctcc tcatgggact atatcacagt aaaaagaggg    420

agtagtcagg acaatagctg tgagggaaaa tgcaaccccc tggttttgca gttcacccag    480

aagggaagac aagcctcttg ggacggacct aagatgtggg gattgcgact ataccgtaca    540
```

-continued

```
ggatatgacc ctatcgcttt attcacggtg tcccggcagg tatcaaccat tacgccgcct    600

caggcaatgg gaccaaacct agtcttacct gatcaaaaac ccccatcccg acaatctcaa    660

acagggtcca aagtggcgac ccagaggccc caaacgaatg aaagcgcccc aaggtctgtt    720

gcccccacca ccatgggtcc caaacggatt gggaccggag ataggttaat aaatttagta    780

caagggacat acctagcctt aaatgccacc gaccccaaca aaactaaaga ctgttggctc    840

tgcctggttt ctcgaccacc ctattacgaa gggattgcaa tcttaggtaa ctacagcaac    900

caaacaaacc cccccccatc ctgcctatct actccgcaac acaaactaac tatatctgaa    960

gtatcagggc aaggaatgtg catagggact gttcctaaaa cccaccaggc tttgtgcaat   1020

aagacacaac agggacatac aggggcgcac tatctagccg cccccaacgg cacctattgg   1080

gcctgtaaca ctggactcac cccatgcatt tccatggcgg tgctcaattg gacctctgat   1140

ttttgtgtct taatcgaatt atggcccaga gtgacttacc atcaacccga atatgtgtac   1200

acacattttg ccaaagctgt caggttccga aga                                 1233
```

```
<210> SEQ ID NO 8
<211> LENGTH: 411
<212> TYPE: PRT
<213> ORGANISM: Feline leukemia virus

<400> SEQUENCE: 8

Asn Pro Ser Pro His Gln Ile Tyr Asn Val Thr Trp Val Ile Thr Asn
1               5                   10                  15

Val Gln Thr Asn Thr Gln Ala Asn Ala Thr Ser Met Leu Gly Thr Leu
            20                  25                  30

Thr Asp Ala Tyr Pro Thr Leu His Val Asp Leu Cys Asp Leu Val Gly
        35                  40                  45

Asp Thr Trp Glu Pro Ile Val Leu Asn Pro Thr Asn Val Lys His Gly
    50                  55                  60

Ala Arg Tyr Ser Ser Ser Lys Tyr Gly Cys Lys Thr Thr Asp Arg Lys
65                  70                  75                  80

Lys Gln Gln Gln Thr Tyr Pro Phe Tyr Val Cys Pro Gly His Ala Pro
                85                  90                  95

Ser Leu Gly Pro Lys Gly Thr His Cys Gly Gly Ala Gln Asp Gly Phe
            100                 105                 110

Cys Ala Ala Trp Gly Cys Glu Thr Thr Gly Glu Ala Trp Trp Lys Pro
        115                 120                 125

Thr Ser Ser Trp Asp Tyr Ile Thr Val Lys Arg Gly Ser Ser Gln Asp
    130                 135                 140

Asn Ser Cys Glu Gly Lys Cys Asn Pro Leu Val Leu Gln Phe Thr Gln
145                 150                 155                 160

Lys Gly Arg Gln Ala Ser Trp Asp Gly Pro Lys Met Trp Gly Leu Arg
                165                 170                 175

Leu Tyr Arg Thr Gly Tyr Asp Pro Ile Ala Leu Phe Thr Val Ser Arg
            180                 185                 190

Gln Val Ser Thr Ile Thr Pro Pro Gln Ala Met Gly Pro Asn Leu Val
        195                 200                 205

Leu Pro Asp Gln Lys Pro Pro Ser Arg Gln Ser Gln Thr Gly Ser Lys
    210                 215                 220

Val Ala Thr Gln Arg Pro Gln Thr Asn Glu Ser Ala Pro Arg Ser Val
225                 230                 235                 240

Ala Pro Thr Thr Met Gly Pro Lys Arg Ile Gly Thr Gly Asp Arg Leu
```

-continued

```
                245                 250                 255

Ile Asn Leu Val Gln Gly Thr Tyr Leu Ala Leu Asn Ala Thr Asp Pro
            260                 265                 270

Asn Lys Thr Lys Asp Cys Trp Leu Cys Leu Val Ser Arg Pro Pro Tyr
        275                 280                 285

Tyr Glu Gly Ile Ala Ile Leu Gly Asn Tyr Ser Asn Gln Thr Asn Pro
    290                 295                 300

Pro Pro Ser Cys Leu Ser Thr Pro Gln His Lys Leu Thr Ile Ser Glu
305                 310                 315                 320

Val Ser Gly Gln Gly Met Cys Ile Gly Thr Val Pro Lys Thr His Gln
                325                 330                 335

Ala Leu Cys Asn Lys Thr Gln Gln Gly His Thr Gly Ala His Tyr Leu
            340                 345                 350

Ala Ala Pro Asn Gly Thr Tyr Trp Ala Cys Asn Thr Gly Leu Thr Pro
        355                 360                 365

Cys Ile Ser Met Ala Val Leu Asn Trp Thr Ser Asp Phe Cys Val Leu
    370                 375                 380

Ile Glu Leu Trp Pro Arg Val Thr Tyr His Gln Pro Glu Tyr Val Tyr
385                 390                 395                 400

Thr His Phe Ala Lys Ala Val Arg Phe Arg Arg
                405                 410


<210> SEQ ID NO 9
<211> LENGTH: 1575
<212> TYPE: DNA
<213> ORGANISM: Artificial Sequence
<220> FEATURE:
<223> OTHER INFORMATION: codon optimized for human

<400> SEQUENCE: 9

atggtgccgc aggctctcct gtttgtcccc cttctggtct ttccattgtg ttttgggaaa     60

ttccctatct acacaattcc ggacaagttg ggaccctgga gcccaattga cattcatcat    120

ctcagctgcc cgaacaattt ggtcgtggag gacgaaggat gcaccaacct gtcggggttc    180

tcctacatgg aattgaaagt cggatacatc agtgccatta agatgaacgg gttcacttgc    240

acaggcgtcg tgactgaagc tgagacatac actaacttcg tgggatatgt cactaccact    300

ttcaaaagaa agcatttccg ccctactcct gatgcttgta gggccgcata caactggaag    360

atggccggtg accccagata tgaggaatca cttcacaatc cgtaccctga ctaccactgg    420

cttcggactg tcaaaaccac caaggagtca ctcgtgatca ttagtccaag tgtggctgat    480

cttgacccat acgaccggtc acttcactca cgggtgttcc cggggggga ttgctctggt    540

gtcgcagtgt cgtcaaccta ctgctccaca aaccacgatt acaccatttg gatgccagaa    600

aatcctcggc ttggtatgtc atgtgacatt ttcaccaatt ctcgggggaa gagggcttcc    660

aaagggtctg aaacttgcgg ctttgtcgat gagcggggct tgtataagtc acttaaaggt    720

gcttgcaaac tcaagctttg tggtgtcttg ggattgagat tgatggatgg aacttgggtc    780

gcaatgcaga cttctaacga aaccaaatgg tgccctcccg gacagcttgt gaatttgcat    840

gactttcgct ctgacgaaat tgagcatctt gtcgtcgagg agttggtcaa gaagcgggaa    900

gagtgtctgg atgctttgga atcaatcatg accaccaagt cagtgtcttt cagacggctc    960

tcacatctta ggaaattggt gccaggtttt ggaaaagcat ataccatttt caacaagacc   1020

cttatggaag ccgatgctca ctacaagtct gtcaggactt ggaatgagat catcccgtct   1080

aaagggtgtc ttagggtcgg agggagatgt catcctcatg tcaacggagt ctttttcaat   1140
```

```
ggtatcattc ttggacctga cggaaatgtc cttatccctg agatgcaatc ttccctcctc   1200

cagcaacaca tggaacttct tgtctcatcg gtcatccccc ttatgcaccc cctggctgac   1260

ccatcaaccg tgttcaagaa cggtgacgag gcagaggatt ttgtcgaggt ccaccttccc   1320

gatgtgcatg aacggatctc tggtgtcgac cttggactcc ctaactgggg aaagtatgtc   1380

cttctgtcgg caggagccct gactgccttg atgttgatta tcttcctgat gacttgttgg   1440

aggagagtca atcggtcgga gccaacacaa cataatctca gaggaacagg aagggaggtg   1500

tcagtcacac cccaaagcgg gaagatcatt tcgtcttggg agtcatacaa gagcggaggt   1560

gaaaccggac tgtga                                                    1575


<210> SEQ ID NO 10
<211> LENGTH: 524
<212> TYPE: PRT
<213> ORGANISM: Rabies virus

<400> SEQUENCE: 10

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Gly Gly
                165                 170                 175

Asn Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
        275                 280                 285
```

His Leu Val Val Glu Glu Leu Val Lys Lys Arg Glu Glu Cys Leu Asp
290 295 300

Ala Leu Glu Ser Ile Met Thr Thr Lys Ser Val Ser Phe Arg Arg Leu
305 310 315 320

Ser His Leu Arg Lys Leu Val Pro Gly Phe Gly Lys Ala Tyr Thr Ile
325 330 335

Phe Asn Lys Thr Leu Met Glu Ala Asp Ala His Tyr Lys Ser Val Arg
340 345 350

Thr Trp Asn Glu Ile Ile Pro Ser Lys Gly Cys Leu Arg Val Gly Gly
355 360 365

Arg Cys His Pro His Val Asn Gly Val Phe Phe Asn Gly Ile Ile Leu
370 375 380

Gly Pro Asp Gly Asn Val Leu Ile Pro Glu Met Gln Ser Ser Leu Leu
385 390 395 400

Gln Gln His Met Glu Leu Leu Val Ser Ser Val Ile Pro Leu Met His
405 410 415

Pro Leu Ala Asp Pro Ser Thr Val Phe Lys Asn Gly Asp Glu Ala Glu
420 425 430

Asp Phe Val Glu Val His Leu Pro Asp Val His Glu Arg Ile Ser Gly
435 440 445

Val Asp Leu Gly Leu Pro Asn Trp Gly Lys Tyr Val Leu Leu Ser Ala
450 455 460

Gly Ala Leu Thr Ala Leu Met Leu Ile Ile Phe Leu Met Thr Cys Trp
465 470 475 480

Arg Arg Val Asn Arg Ser Glu Pro Thr Gln His Asn Leu Arg Gly Thr
485 490 495

Gly Arg Glu Val Ser Val Thr Pro Gln Ser Gly Lys Ile Ile Ser Ser
500 505 510

Trp Glu Ser Tyr Lys Ser Gly Gly Glu Thr Gly Leu
515 520

<210> SEQ ID NO 11
<211> LENGTH: 13
<212> TYPE: DNA
<213> ORGANISM: Artificial Sequence
<220> FEATURE:
<223> OTHER INFORMATION: 5 'flanking sequence

<400> SEQUENCE: 11
ggcgcgccgc acc 13

<210> SEQ ID NO 12
<211> LENGTH: 1638
<212> TYPE: RNA
<213> ORGANISM: Artificial Sequence
<220> FEATURE:
<223> OTHER INFORMATION: codon optimized for feline

<400> SEQUENCE: 12
auggcugacg acggaucugu gaccacccca gaacaaggaa caauggucgg aggagugauu 60
gccgaaccca gcgcucagau gucaacugcg gcggacaugg ccuccggaaa gucgguggac 120
uccgaguggg aagccuucuu cucguuccac acguccguga acuggagcac cuccgaaacc 180
caaggaaaga uccucuucaa gcagucccug gguccccugc ugaacccgua ccuggagcac 240
aucagcaagc uguacgucgc uuggagcggg ucgaucgaag ugcgauuuuc caucucggga 300
agcggcgugu ucgguguaa acuggccgcc aucgucgugc cgccuggugu cgacccuguc 360

-continued

```
cagucaaccu ccaugcugca guacccgcac guccuguucg acgcaagaca aguggagcca    420
gugaucuucu ccaucccgga ccuccgcaac agccuguauc acuugauguc cgauaccgau    480
accacuuccc ucgugaucau gguguacaac gaucugauca acccguacgc caaugacucc    540
aacagcucgg guugcaucgu gaccgucgaa acgaagccug gcaucgauuu caaguuucau    600
cugcugaaac cgcccggauc caugcuuacu cacgggucca ucccuuccga ucugaucccc    660
aagagcuccu cccuguggau ugggaaccgc cacuggaccg auauuaccga uuucgugauu    720
cggccuuucg uguuccaagc caaccggcac uucgacuuca accaggagac ugccggcugg    780
ucaacuccac gguuccgccc auuggccgug acugugucgc agucaaaggg agccaagcuc    840
gggaacggca ucgccaccga cuacauugug ccuggaaucc ccgacggaug gccugauacu    900
accaucccca ccaagcugac cccuaccgga gauuacgcca ucaccuccuc cgacggcaau    960
gauauugaaa ccaagcugga auacgagaac gcggacguga uuaagaacaa caccaacuuc   1020
cgcuccaugu auaucugcgg aagccuccag agggcuuggg gcgacaagaa gaucagcaac   1080
accggguuca ucacuaccgg agugauuucu gacaacucca ucagcccuuc gaacacaauu   1140
gaccagucca agaucguggu guaccaggac aaccauguca auucggaggu ccagacuagc   1200
gacaucacuc uugccauccu gggcuacacc ggaauuggag aagaggccau aggcgccaac   1260
cgggacuccg ucgugagaau uuccgugcuu ccggaaacug gagcaagggg cggaaaucac   1320
cccaucuucu acaaaaauuc caugaagcug ggcuacguga ucuccuccau ugacguguuc   1380
aacucccaaa uccuccacac cucgcgccag cugucacuga acaacuacuu guugcccccu   1440
gacuccuucg cgguguaccg gauuauugac agcaacggau caugguucga cauugggauu   1500
gacagcgaug gguuuucauu cgugggcgug ucgucauuuc caaagcugga guuuccgcug   1560
uccgccucau acaugggcau ccagcucgca aagauccggc uggcguccaa cauccgguca   1620
uccaugacua agcuguga                                                1638
```

<210> SEQ ID NO 13
<211> LENGTH: 1629
<212> TYPE: RNA
<213> ORGANISM: Artificial Sequence
<220> FEATURE:
<223> OTHER INFORMATION: codon optimized for feline

<400> SEQUENCE: 13

```
augacugccc cggaacaagg aacgaugguc ggaggaguga uugcagaacc gucagcacag     60
auguccaccg cugccgacau ggccacugga aagagcgugg acuccgaaug ggaagccuuc    120
uucuccuucc acacuucggu caacuggucg acuagcgaaa cccaggggaa gauuuuguuc    180
aagcaauccc ucggcccucu gcugaacccc uaccuggagc aucuggccaa gcuguacgug    240
gcauggucgg gcagcaucga agugcgcuuu agcauuuccg gcuccggagu guucgggggga    300 aagcuugcug ccauugucgu gccgccagga guggacccgg ugcaguccac uucuaugcuc    360
caauacccgc auguccuguu cgacgccaga cagguggagc cugugaucuu uugccugccg    420
gaucucaggu ccacccugua ucaccucaug uccgacaccg acaccaccuc gcucgugauc    480
augguguaca acgaccugau caaccccuac gcuaacgacg ccaacagcuc agguugcauu    540
gugacugucg aaaccaagcc aggcccugac uucaaguuuc auuugcugaa gccgcccggu    600
uccaugcuga cccacggcuc gaucccaucc gaccugaucc ccaagacgag cucccugugg    660
aucggaaacc gcuacugguc cgauauuacc gacuucguga ucagaccauu cguguuccaa    720
gccaaccgcc auuucgacuu caaccaggaa accgcaggau ggucgacccc ucgauuccgc    780
```

-continued

```
ccgauuucag ugaccaucac cgaacagaac ggcgcgaagc ugggaauugg cguggcgacc    840

gacuacaucg ugccgggaau cccggaugga uggccugaua cgaccauucc cggggagcug    900

aucccugccg gggacuacgc caucaccaac gguacuggaa acgacaucac cacugccacc    960

gguuacgaca ccgccgacau cauaaagaac aacaccaacu ucagaggaau guacauuugc   1020

ggcucccugc aacgcgcuug gggugacaaa aagaucucga acacugccuu caucacaaca   1080

gcgacucugg acggcgauaa caacaacaag aucaauccuu guaauaccau cgaccagucc   1140

aaaaucgugg uguuccagga uaaccacgug ggaaagaagg cgcagaccuc cgacgacacu   1200

cuggcgcugc uuggcuacac cgggaucggc gagcaggcca uuggaagcga ucgggaucgg   1260

gucgugcgga ucuccacccu ccccgagacu ggagcaaggg gaggcaacca ccccaucuuu   1320

uacaaaaaca gcauuaagcu cggauacguc auccgcucca ucgauguguu caacucucaa   1380

auccugcaca cuucgcggca gcugucccug aaccacuacc ucuugccgcc cgacuccuuc   1440

gccgucuacc ggaucauuga uucgaacggg agcugguucg acaucggcau ugauagcgau   1500

ggcuucucgu uugugggcgu gucgggcuuc gggaagcugg aguucccacu gagcgccuca   1560

uacaugggua uccagcuggc caagaucagg cuggccucca acauccgcuc accuaugacu   1620

aagcuguga                                                           1629
```

<210> SEQ ID NO 14
<211> LENGTH: 1929
<212> TYPE: RNA
<213> ORGANISM: Artificial Sequence
<220> FEATURE:
<223> OTHER INFORMATION: codon optimized for feline

<400> SEQUENCE: 14

```
auggagucac caacacaccc uaaaccuucu aaagacaaaa cccucucgug gaaucucgcc     60

uuccuugugg gcauccuguu cacaaucgac aucggcaugg ccaacccuuc gccgcaucag    120

aucuacaaug ugacaugggu cauuacuaau gugcagacaa acacccaggc aaaugcuacu    180

ucuaugcuug guacucugac ugaugcuuau ccaacccugc acgucgaccu uugcgaucuc    240

gucggugaca caugggagcc caucgugcug aauccaacua augucaaaca uggugccagg    300

uauucuucua gcaaauacgg guguaagacc acugaucgga agaaacagca acaaaccuac    360

ccauucuacg ugugcccggg ucacgcaccg ucccuggguc cgaagggaac acauugugg     420

ggagcccaag acgguuuuug cgcugcuugg gguugugaaa caaccggaga agccuggugg    480

aagccuaccu caucuuggga cuacauuacu gugaaaagag gcucuagcca ggauaacagc    540

ugcgaaggaa aguguaaucc ccugguguu caauucaccc agaaaggccg gcaggcauca     600

ugggauggac cgaaaaugug gggacuuaga cucuaucgca ccggauacga ccccaucgcu    660

cuguuuacug ugucacgcca agucuccacc auuacuccgc cacaggccau ggggccgaau    720

cugguccucc ccgaucagaa gccacccuca cggcaaaguc aaaccggcuc aaaaguggcc    780

acccaacggc cccagacaaa ugaguccgca ccuaggucag uggcaccuac aacaaugggu    840

ccaaagcgga ucggaaccgg agacaggcuc auuaaccucg ugcaagggac uuaucuggcc    900

cuuaacgcua cugaccccaa caagaccaag gauugcuggc ucugccuugu gagcagaccu    960

ccuuacuaug aggggaucgc cauucucgga aacuacucaa aucagaccaa ccccccuccg   1020

ucgugucuga gcaccccca gcacaagcuu acuauuucag aagucagugg acagggaaug    1080

ugcaucggaa ccgugccaaa gacucaucaa gcccuuugca acaaaacuca acaagggcac   1140
```

-continued

```
acuggagcuc auuaucucgc cgcaccuaac gggaccuacu gggcuugcaa uacuggauug   1200

accccgugua ucucuauggc cgugcugaau uggacuuccg acuucugcgu gcuuauugag   1260

cuuuggccua gagugacaua ccaucagccu gaguacgucu auacccauuu cgccaaggca   1320

gucagauucc ggcgggagcc uaucucccug acuguggccu ugaugcucgg uggacugaca   1380

gugggaggaa uugcagcugg agucggaacu ggaaccaagg cccugcucga aacugcucag   1440

uuccggcagc ugcagauggc caugcacacu gacauccagg cucuggagga aucaauuuca   1500

gcccuugaga aaagcuugac cucgcugucu gaaguggucc uccaaaacag gcgcgguuug   1560

gacauccugu uccuucaaga ggguggucug ugcgccgcuc ucaaggagga augcuguuuc   1620

uacgcugacc auaccgggcu ggugcgcgau aacauggcaa agcugcggga acgcuugaaa   1680

cagaggcagc aacuguucga cucucagcag ggaugguucg agggcugguu uaacaagagc   1740

ccaugguuua ccacucugau cucuucaauc augggucccac ugcucauccu gcuucugauu   1800

cuucucuucg gaccguguau ucucaacagg cuggugcagu uugucaagga cagaaucucg   1860

gugguccagg cccugauucu uacucagcag uaucagcaga uuaagcagua cgaccccgau   1920

cggccuuga                                                            1929


<210> SEQ ID NO 15
<211> LENGTH: 1233
<212> TYPE: RNA
<213> ORGANISM: Artificial Sequence
<220> FEATURE:
<223> OTHER INFORMATION: codon optimized for feline

<400> SEQUENCE: 15

aauccuaguc cacaccaaau auauaaugua acuuggguaa uaaccaaugu acaaacuaac     60

acccaagcua acgccaccuc uauguuagga accuuaaccg augccuaccc uacccuacau    120

guugacuuau gugaccuagu gggagacacc ugggaaccua uaguccuaaa cccaaccaau    180

guaaaacacg gggcacguua cuccuccuca aaauauggau guaaaacuac agauagaaaa    240

aaacagcaac agacauaccc cuuuuacguc ugccccggac augcccccuc guuggggcca    300

aagggaacac auuguggagg ggcacaagau ggguuuugug ccgcaugggg augugagacc    360

accggagaag cuugguggaa gcccaccucc ucaugggacu auaucacagu aaaaagaggg    420

aguagucagg acaauagcug ugagggaaaa ugcaaccccc ugguuuugca guucacccag    480

aagggaagac aagccucuug ggacggaccu aagaugungg gauugcgacu auaccguaca    540

ggauaugacc cuaucgcuuu auucacggug ucccggcagg uaucaaccau uacgccgccu    600

caggcaaugg gaccaaaccu agucuuaccu gaucaaaaac cccaucccg acaaucucaa    660

acagggucca aaguggcgac ccagaggccc caaacgaaug aaagcgcccc aaggucuguu    720

gcccccacca ccaugggucc caaacggauu gggaccggag auagguuaau aaauuuagua    780

caagggacau accuagccuu aaaugccacc gaccccaaca aaacuaaaga cuguuggcuc    840

ugccugguuu cucgaccacc cuauuacgaa gggauugcaa ucuuagguaa cuacagcaac    900

caaacaaacc cccccccauc cugccuaucu acuccgcaac acaaacuaac uauaucugaa    960

guaucagggc aaggaaugug cauagggacu guuccuaaaa cccaccaggc uuugugcaau   1020

aagacacaac agggacauac aggggcgcac uaucuagccg cccccaacgg caccuauugg   1080

gccuguaaca cuggacucac cccaugcauu uccauggcgg ugcucaauug gaccucugau   1140

uuuugugucu uaaucgaauu auggcccaga gugacuuacc aucaacccga auauguguac   1200

acacauuuug ccaaagcugu cagguuccga aga                                1233
```

-continued

```
<210> SEQ ID NO 16
<211> LENGTH: 1575
<212> TYPE: RNA
<213> ORGANISM: Artificial Sequence
<220> FEATURE:
<223> OTHER INFORMATION: codon optimized for human

<400> SEQUENCE: 16

auggugccgc aggcucuccu guuugucccc cuucuggucu uuccauugug uuuugggaaa     60

uucccuaucu acacaauucc ggacaaguug ggacccugga gcccaauuga cauucaucau    120

cucagcugcc cgaacaauuu ggucguggag gacgaaggau gcaccaaccu gucgggguuc    180

uccuacaugg aauugaaagu cggauacauc agugccauua agaugaacgg guucacuugc    240

acaggcgucg ugacugaagc ugagacauac acuaacuucg ugggauaugu cacuaccacu    300

uucaaaagaa agcauuuccg cccuacuccu gaugcuugua gggccgcaua caacuggaag    360

auggccggug accccagaua ugaggaauca cuucacaauc cguacccuga cuaccacugg    420

cuucggacug ucaaaaccac caaggaguca cucgugauca uuaguccaag uguggcugau    480

cuugacccau acgaccgguc acuucacuca cgggguguucc cgggggggaa uugcucuggu    540

gucgcagugu cgucaaccua cugcuccaca aaccacgauu acaccauuug gaugccagaa    600

aauccucggc uugguauguc augugacauu uucaccaauu cucgggggaa gagggcuucc    660

aaagggucug aaacuugcgg cuuugucgau gagcggggcu uguauaaguc acuuaaaggu    720

gcuugcaaac ucaagcuuug uggugucuug ggauugagau ugauggaugg aacuuggguc    780

gcaaugcaga cuucuaacga aaccaaaugg ugcccucccg gacagcuugu gaauuugcau    840

gacuuucgcu cugacgaaau ugagcaucuu gucgucgagg aguuggucaa gaagcgggaa    900

gagugucugg augcuugga aucaaucaug accaccaagu cagugucuuu cagacggcuc    960

ucacaucuua ggaaauuggu gccagguuuu ggaaaagcau auaccauuuu caacaagacc   1020

cuuauggaag ccgaugcuca cuacaagucu gucaggacuu ggaaugagau caucccgucu   1080

aaagggguguc uuagggucgg agggagaugu cauccucaug ucaacggagu cuuuuucaau   1140

gguaucauuc uuggaccuga cggaaauguc cuuaucccug agaugcaauc uucccuccuc   1200

cagcaacaca uggaacuucu ugucucaucg gucauccccc uuaugcaccc ccuggcugac   1260

ccaucaaccg uguucaagaa cggugacgag gcagaggauu uugucgaggu ccaccuuccc   1320

gaugugcaug aacggaucuc uggugucgac cuuggacucc cuaacugggg aaaguauguc   1380

cuucugucgg caggagcccu gacugccuug auguugauua ucuuccugau gacuuguugg   1440

aggagaguca aucggucgga gccaacacaa cauaaucuca gaggaacagg aagggaggug   1500

ucagucacac cccaaagcgg gaagaucauu ucgucuuggg agucauacaa gagcggaggu   1560

gaaaccggac uguga                                                    1575
```

MULTIVALENT FELINE VACCINE

CROSS-REFERENCE TO RELATED APPLICATIONS

This application is a national stage entry under 35 U.S.C. § 371 of PCT/EP2018/080106, filed on Nov. 5, 2018, which claims priority under 35 U.S.C. § 119(e) of provisional application U.S. Ser. No. 62/599,401 filed Dec. 15, 2017, 62/596,508 filed Dec. 8, 2017, U.S. Ser. No. 62/582,050, filed Nov. 6, 2017, and U.S. Ser. No. 62/581,955 filed Nov. 6, 2017, the contents of which are hereby incorporated by reference in their entireties.

FIELD OF THE INVENTION

The present invention relates to new multivalent vaccines for felines. Methods of making and using the multivalent vaccines alone or in combination with other protective agents are also provided.

BACKGROUND

Feline respiratory disease includes those illnesses typified by rhinosinusitis, conjunctivitis, lacrimation, salivation, and oral ulcerations. The two most common pathogens associated with upper respiratory disease in cats are feline calicivirus (FCV) and feline viral rhinotracheitis virus (FVR), which is also known as feline herpesvirus type 1 virus (FHV-1). These two feline viruses are considered responsible for approximately 80% of all feline respiratory disease, worldwide. A bacterium, *Chlamydophila felis*, is a third pathogen that also can play a role in feline respiratory disease. Accordingly, vaccines against these three pathogens are now commercially available.

FVR is an alphaherpesvirus that is related to canine herpesvirus-1 and is perhaps the most important of the cat respiratory pathogens. FVR is a large, enveloped DNA virus that is extremely contagious and can lead to severe disease in kittens, as well as cats. Accordingly, most cats are exposed to FVR during their lifetime. The commercially available Nobivac® Feline-1 vaccine contains a modified live feline viral rhinotracheitis virus.

The most common characteristic and clinical signs of FCV infection are the development of vesicles (ulcers) on the tongue and oral mucosa, which begin as small, individual, ulcers but can spread and affect a large part of the tongue. Fever often also is observed in infected cats. Certain strains of FCV also cause a disease in cats known as limping syndrome, which is characterized by fever, joint and muscle soreness (limping), and occasional lingual/oral ulceration. In addition, some strains of FCV have been associated with chronic stomatitis in infected cats. Cats infected with FCV may become persistently infected, and may shed infectious virus for long periods of time.

FCV isolates are antigenically highly variable, and antibodies from cats vaccinated with older vaccine strains of FCV, such as FCV F9, do not efficiently neutralize all current field isolates. Moreover, new FCV strains associated with systemic disease and high mortality have been identified [see e.g., U.S. Pat. No. 7,449,323 B2]. These "virulent systemic" (VS-FCV) isolates are responsible for localized outbreaks, and current vaccines also do not appear to protect cats from disease caused by these strains.

FCV comprises a single-stranded, positive-sense RNA genome consisting of three open reading frames (ORFs). The genome is polyadenylated at the 3' end and bound by a virally-encoded protein at the 5'-end. The first open reading frame encodes a viral protease and an RNA-dependent RNA polymerase, which are expressed on a single polypeptide. This polypeptide then is post-translationally cleaved by the viral protease. The second open reading frame encodes the major capsid protein (i.e., the FCV capsid protein), which has six regions denoted as A-F [Scott et al., 60 *Am. J. Vet. Res.*:652-658 (1999)]. Region A is cleaved to produce the mature capsid protein. Whereas regions B, D, and F of ORF2 are relatively conserved between FCV isolates, regions C and E are variable, with region E of ORF2 containing the major B-cell epitopes [see, Radford et al., 38(2) *Vet Res.*: 319-335 (2007)]. ORF 3 encodes a minor structural protein [Sosnovtsev and Green, 277 *Virology:* 193-203 (2000)].

*Chlamydophila felis* is a bacterium that is endemic among domestic cats worldwide. *C. felis* can lead to inflammation of conjunctiva, rhinitis, and respiratory problems in the infected cat *C. felis* has a relatively small genome that encodes only about a thousand proteins. This bacterium also contains a plasmid comprising 75,000 base pairs. The commercially available Nobivac® Feline-1 vaccine contains a modified live *Chlamydophila felis*.

In addition to the three pathogens related to feline respiratory disease discussed above, cats often also are vaccinated against three other viruses: feline leukemia virus (FeLV), feline panleukopenia (FPV or FPLV), and rabies virus. Feline leukemia virus is a retrovirus that infects domestic cats, resulting in significant morbidity and mortality worldwide. Though predominantly transmitted through saliva, FeLV has been reported also to be spread through contact with body fluids [Pacitti et al., *Vet Rec* 118:381-384 (1986) doi:10.1136/vr.118.14.381; Levy et al., *J Feline Med Surg* 10:300-316 (2008) doi:10.1016/j.jfms.2008.03.002]. The clinical signs in cats observed during FeLV infections include: cytoproliferative disorders (lymphoid or myeloid tumors), cytosuppressive disorders (infectious diseases associated with immunosuppression, anemia, myelosuppression), inflammatory disorders, neurological disorders, abortions, and enteritis [Hoover et al., *J Am Vet Med Assoc* 199:1287-1297 (1991); Levy and Crawford, *Textbook of Veterinary Internal Medicine,* 6th ed (Ettinger S J, Feldman E C., eds.) WB Saunders, Philadelphia, Pa. (2005)]. The prevalence of antigenemia may vary from 1-5% in healthy cats to 15-30% in afflicted cats [Hosie et al. *Veterinary Records,* 128: 293-297 (1989); Braley, *Feline Practice* 22: 25-29 (1994); Malik et al., *Australian Veterinary Journal* 75:323-327 (1997); Arjona et al., *Journal of Clinical Microbiology* 38:3448-3449 (2000)]. FeLV frequently establishes a lasting infection with a concomitant persistent viremia, often leading to the death of the host cat.

The single stranded RNA genome of FeLV encodes only three genes: (i) an ENV gene, which encodes the envelope glycoprotein, (ii) a GAG gene, which encodes the major structural components of the virus, and (iii) a POL gene, which encodes the RNA polymerase [Thomsen et al., *Journal of General Virology* 73:1819-1824 (1992)]. The FeLV envelope (ENV) gene encodes a gp85 precursor protein which is proteolytically processed by one or more cellular enzymes to yield the major envelope glycoprotein gp70 and the associated transmembrane protein p15E [DeNoronha, et al., *Virology* 85:617-621 (1978); Nunberg et al., *PNAS* 81:3675-3679 (1983)]. The transmembrane protein p15E contains a sequence conserved among gammaretroviruses with immunosuppressive properties [Mathes et al., *Nature* 274:687-689 (1978)]. Recently, The European Medicines Agency's Committee for Medicinal Products for Veterinary Use (CVMP) has adopted a positive opinion for a vaccine comprising a recombinant p45 FeLV-envelope antigen derived from the gp70 surface glycoprotein of the FeLV subgroup A that is expressed in *Escherichia coli* as active substance. The FeLV envelope glycoprotein is the target of FeLV-specific cytotoxic T cell responses, as well as neutralizing antibodies and accordingly, one of the major immunogens of FeLV [Flynn et al., *J. Virol.* 76(5): 2306-2315 (2002)].

Feline panleukopenia (FPV or FPLV) is a highly contagious viral disease of cats that is often fatal. The name panleukopenia derives from the low white blood cell count (leucocytes) exhibited by affected animals. FPLV infects and destroys actively dividing cells in lymphoid tissues, bone marrow, intestinal epithelium, and in very young kittens, the retina and cerebellum. The virus also may spread in pregnant cats transplacentally to cause embryonic resorption, fetal mummification, stillbirth, or abortion. Infected cats shed the virus in their urine, stool, and nasal secretions resulting in infection in susceptible cats when they come in contact with these secretions or fleas from infected cats. The clinical signs due to an FPLV infection have also been labeled as feline distemper or feline parvo.

Feline panleukopenia virus is a member of the genus *Parvovirus*, in the family Parvoviridae. Accordingly, FPLV is closely related to mink enteritis virus and canine Type 2 parvovirus (CPV-2). FPLV has a single stranded DNA genome that has been sequenced [see, Liu et al., *Genome Announc*. March-April; 3(2) (2015): e01556-14]. The commercially available Nobivac® Feline-1 vaccine contains a modified live feline panleukopenia virus.

Rabies is a preventable zoonotic disease that leads to inflammation of the brain in humans and other mammals. Clinical rabies is an acute, progressive encephalitis that is typically classified as either furious or paralytic rabies. Furious rabies is characterized by restlessness, irritability and aggression. Paralytic rabies is characterized by excessive salivation, deep, labored breathing, paralysis, and eventually coma. The causative agent of rabies is the rabies virus, which is capable of infecting most mammals, including felines, and maintains a reservoir of disease in wild and susceptible domestic animals.

The rabies virus is an enveloped, RNA virus that encodes five structural proteins: a nucleoprotein (N), a phosphoprotein (P), a matrix protein (M), a glycoprotein (G), and an RNA-dependent RNA polymerase [Dietzschold et al., *Crit Rev Immunol* 10:427-439 (1991)]. The glycoprotein (G) is considered the protective antigen which induces virus neutralizing antibodies [Cox et al., *Infect Immun* 16:754-759 (1977)]. Several types of rabies vaccines have been produced to combat this disease. Inactivated cell culture derived whole-virus killed rabies virus vaccines are the most commonly used vaccines in the United States. These whole-virus killed rabies virus vaccines require high levels of antigen and therefore, require an adjuvant. Unfortunately, this use of an adjuvant is associated with injection site reactivity, hypersensitivity, and even with the perceived risk of injection site sarcomas in cats. Recently, a modified live vaccine has been used successfully with oral vaccine baits for the immunization of wild animals [Mahl et al., *Vet Res* 45(1):77 (2014)]. In addition, a recombinant vaccine expressing the glycoprotein (G) is currently being marketed in the United States for use in cats. Nucleic acid vaccines also have been used in laboratory studies, though none are currently licensed in the United States.

A number of vector strategies have been employed through the years for vaccines in an effort to protect against certain pathogens. One such vector strategy includes the use of alphavirus-derived replicon RNA particles (RP) [Vander Veen, et al. *Anim Health Res Rev.* 13(1):1-9. (2012) doi: 10.1017/S1466252312000011; Kamrud et al., *J Gen Virol.* 91(Pt 7):1723-1727 (2010)] which have been developed from several different alphaviruses, including Venezuelan equine encephalitis virus (VEE) [Pushko et al., *Virology* 239:389-401 (1997)], Sindbis (SIN) [Bredenbeek et al., *Journal of Virology* 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. *Anim Health Res Rev.* 13(1):1-9. (2012)]. The RP platform has been used to encode pathogenic antigens and is the basis for several USDA-licensed vaccines for swine and poultry.

Notably, alphavirus RNA replicon particles, and in particular Venezuelan Equine Encephalitis (VEE) alphavirus RNA replicon particles, have been reported to catalyze a systemic antiviral state and protect against lethal virus challenge [Konopka et al., *J. Virol.,* 83 (29):12432-12442 (2009)] and more particularly, induce rapid protection against foot-and-mouth disease virus [Segundo et al., *J. Virol.,* 87 (10):5447-5460 (2013)]. Accordingly, because alphavirus RNA replicon particles enhance the innate immune response against live virus it would appear that they should not be combined with a modified live virus in a vaccine because it would be expected to be detrimental to the immune response.

The citation of any reference herein should not be construed as an admission that such reference is available as "prior art" to the instant application.

SUMMARY OF THE INVENTION

Accordingly, the present invention includes immunogenic compositions that comprise alphavirus RNA replicon particles that encode one or more antigens from one or more feline pathogens along with one or more modified live feline pathogens. All of the immunogenic compositions of the present invention also may be used in multivalent vaccines. In a particular embodiment of this type, the vaccinated subject is a feline. In a more particular embodiment, the vaccinated subject is a domestic cat. Methods of making and using the immunogenic compositions and vaccines of the present invention are also provided.

In particular embodiments, the immunogenic compositions comprise alphavirus RNA replicon particles that encode one or more feline calicivirus (FCV) antigens and a modified live feline pathogen. In other embodiments, the immunogenic compositions comprise alphavirus RNA replicon particles that encode one or more feline leukemia virus (FeLV) antigens and a modified live feline pathogen. In yet other embodiments, the immunogenic compositions comprise alphavirus RNA replicon particles that encode one or more rabies virus antigens and a modified live feline pathogen. In certain embodiments, the modified live feline pathogen is a feline viral rhinotracheitis virus (FVR). In other embodiments, the modified live feline pathogen is a feline panleukopenia virus (FPLV). In yet other embodiments, the modified live feline pathogen is a modified live *Chlamydophila felis*. In still other embodiments, the modified live feline pathogen is a modified live F9-like feline calicivirus (FCV F9-Like). In yet other embodiments, the modified live feline pathogen is a modified live *Bordetella bronchiseptica*.

The present invention further provides immunogenic compositions that comprise any combination of these alphavirus RNA replicon particles and modified live feline pathogens. In specific embodiments of this type, the immunogenic composition comprises alphavirus RNA replicon particles encoding an FCV antigen, alphavirus RNA replicon particles encoding an FeLV antigen, a modified live FVR, a modified live FPLV, and a modified live *Chlamydophila felis.*

In certain embodiments of this type, the immunogenic compositions comprise alphavirus RNA replicon particles that encode an FCV capsid protein. In more particular embodiments, the FCV capsid protein is an FCV F9-Like capsid protein. In other embodiments, the alphavirus RNA replicon particle encodes an antigenic fragment of an FCV F9-Like capsid protein. In yet other embodiments, the FCV capsid protein is a virulent systemic FCV (VS-FCV) capsid protein. In still other embodiments, the alphavirus RNA replicon particle encodes an antigenic fragment of a VS-FCV capsid protein. In yet other embodiments, the alphavirus RNA replicon particle encodes both an FCV F9-Like capsid protein or antigenic fragment thereof, and an VS-FCV capsid protein or antigenic fragment thereof.

In other embodiments, the immunogenic compositions comprise alphavirus RNA replicon particles that encode a VS-FCV capsid protein or antigenic fragment thereof in which the VS-FCV capsid protein comprises an amino acid sequence comprising 95% identity or more with the amino acid sequence of SEQ ID NO: 2. In more specific embodiments, the VS-FCV capsid protein comprises the amino acid sequence of SEQ ID NO: 2. In even more specific embodiments, the VS-FCV capsid protein is encoded by the nucleotide sequence of SEQ ID NO: 1 or SEQ ID NO: 12. In related embodiments, an alphavirus RNA replicon particle of the present invention encodes a FCV F9-Like capsid protein or antigenic fragment thereof. In specific embodiments of this type, the FCV F9-Like capsid protein comprises an amino acid sequence comprising 95% identity or more with the amino acid sequence of SEQ ID NO: 4. In more specific embodiments, the FCV F9-Like capsid protein comprises the amino acid sequence of SEQ ID NO: 4. In even more specific embodiments of this type, the FCV F9-Like capsid protein is encoded by the nucleotide sequence of SEQ ID NO: 3 or SEQ ID NO: 13.

In related embodiments, the immunogenic compositions comprise alphavirus RNA replicon particles that encode one or more feline leukemia virus (FeLV) antigens. In certain embodiments, the FeLV antigen is a FeLV glycoprotein (e.g., gp85). In other embodiments, the alphavirus RNA replicon particle encodes an antigenic fragment of the FeLV gp85. In more specific embodiments of this type, the antigenic fragment of the FeLV glycoprotein is FeLV gp70. In a related embodiment, the antigenic fragment of the FeLV glycoprotein is FeLV gp45. In more specific embodiments of this type, the FeLV gp85 comprises an amino acid sequence comprising 95% identity or more with the amino acid sequence of SEQ ID NO: 6. In more specific embodiments of this type, the FeLV gp85 comprises the amino acid sequence of SEQ ID NO: 6. In even more specific embodiments of this type, the FeLV gp85 is encoded by the nucleotide sequence of SEQ ID NO: 5 or SEQ ID NO: 14. In related embodiments, the FeLV gp70 comprises an amino acid sequence comprising 95% identity or more with the amino acid sequence of SEQ ID NO: 8. In more specific embodiments of this type, the FeLV gp70 comprises the amino acid sequence of SEQ ID NO: 8. In even more specific embodiments of this type, the FeLV gp70 is encoded by the nucleotide sequence of SEQ ID NO: 7 or SEQ ID NO: 15.

In yet other embodiments the immunogenic compositions comprise alphavirus RNA replicon particles that encode a rabies virus glycoprotein (G). In still other embodiments, the alphavirus RNA replicon particles encode an antigenic fragment of the rabies virus G. In more specific embodiments of this type, the rabies virus G comprises an amino acid sequence comprising 95% identity or more with the amino acid sequence of SEQ ID NO: 10. In still more specific embodiments of this type, the rabies virus G comprises the amino acid sequence of SEQ ID NO: 10. In even more specific embodiments of this type, the rabies virus G is encoded by the nucleotide sequence of SEQ ID NO: 9 or SEQ ID NO: 16.

In particular embodiments, the alphavirus RNA replicon particle is a Venezuelan Equine Encephalitis (VEE) alphavirus RNA replicon particle. In more specific embodiments of this type, the VEE alphavirus RNA replicon particle is a TC-83 VEE alphavirus RNA replicon particle. In other embodiments, the alphavirus RNA replicon particle is a Sindbis (SIN) alphavirus RNA replicon particle. In still other embodiments, the alphavirus RNA replicon particle is a Semliki Forest virus (SFV) alphavirus RNA replicon particle. In an alternative embodiment, a naked DNA vector encodes one or more antigens that originate from one or more feline pathogens. In particular embodiments of this type, the naked DNA vectors encode an FCV capsid protein or antigenic fragment thereof. In specific embodiments of this type, the naked DNA vectors encode an VS-FCV capsid protein or antigenic fragment thereof. In other embodiments of this type, the naked DNA vectors encode an FeLV gp85, or antigenic fragment thereof.

In certain embodiments, the immunogenic compositions can include at least one modified live feline pathogen and alphavirus RNA replicon particles that encode one or more FCV capsid proteins or antigenic fragments thereof, one or more FeLV glycoproteins or antigenic fragments thereof, and/or one or more rabies virus G proteins or antigenic fragments thereof. In particular embodiments of this type, the alphavirus RNA replicon particles encode both a VS-FCV capsid protein or an antigenic fragment thereof, and an FCV F9-Like capsid protein or an antigenic fragment thereof. In related embodiments, the alphavirus RNA replicon particles encode both a VS-FCV capsid protein or an antigenic fragment thereof, and an FeLV gp85 or an antigenic fragment thereof. In other embodiments, the alphavirus RNA replicon particles encode both a FCV F9-Like capsid protein or an antigenic fragment thereof, and an FeLV gp85 or an antigenic fragment thereof. In alternative embodiments, the alphavirus RNA replicon particles encode both a VS-FCV capsid protein or an antigenic fragment thereof, and a rabies virus G protein or an antigenic fragment thereof. In yet other embodiments, the alphavirus RNA replicon particles encode both a FCV F9-Like capsid protein or an antigenic fragment thereof, and a rabies virus G protein or an antigenic fragment thereof. In still other embodiments, the alphavirus RNA replicon particles encode a VS-FCV capsid protein or an antigenic fragment thereof, an FeLV gp85 or an antigenic fragment thereof, and a rabies virus G protein or an antigenic fragment thereof. In alternative embodiments, the alphavirus RNA replicon particles encode a VS-FCV capsid protein or an antigenic fragment thereof, a FCV F9-Like capsid protein or an antigenic fragment thereof, and an FeLV gp85 or an antigenic fragment thereof. In yet other embodiments, the alphavirus RNA replicon particles encode a VS-FCV capsid protein or an antigenic fragment thereof, an FeLV gp85 or an antigenic fragment thereof, a rabies virus G protein or an antigenic fragment thereof, and an FCV F9-Like capsid protein or an antigenic fragment thereof. In still other embodiments, the alphavirus RNA replicon particles encode an FeLV gp85 or an antigenic fragment thereof, and a rabies virus G protein or an antigenic fragment thereof. In yet other embodiments, the alphavirus RNA replicon particles encode an FeLV gp85 or an antigenic fragment thereof, an FCV F9-Like capsid protein or an antigenic fragment thereof, and a rabies virus G protein or an antigenic fragment thereof.

Accordingly, the present invention provides immunogenic compositions that include at least one modified live feline pathogen and any one or more of the alphavirus RNA replicon particles of the present invention that encode multiple feline pathogen antigens, and/or any one or more alphavirus RNA replicon particles of the present invention that encode a single feline pathogen antigen. In particular embodiments, the modified live feline pathogen is a modified live FVR. In other embodiments, the modified live feline pathogen is a modified live FPLV. In yet other embodiments, the modified live feline pathogen is a modified live *Chlamydophila felis*. In still other embodiments, the modified live feline pathogen is a modified live FCV F9-Like. In yet other embodiments, the modified live feline pathogen is a modified live *Bordetella bronchiseptica*. In particular embodiments, two or more modified live feline pathogens are included in the immunogenic composition. In specific embodiments of this type, the immunogenic composition comprises a modified live FVR and a modified live *Chlamydophila*. In other embodiments, three or more modified live feline pathogens are included in the immunogenic composition. In specific embodiments of this type, the immunogenic composition comprises a modified live FVR, a modified live *Chlamydophila*, and a modified live feline pathogen is an FPLV. In still other embodiments, four or more modified live feline pathogens are included in the immunogenic composition. In specific embodiments of this type, the immunogenic composition comprises a modified live FVR, a modified live *Chlamydophila*, a modified live FPLV, and a modified live F9-Like FCV. In particular embodiments, all of the alphavirus RNA replicon particles in the immunogenic composition are Venezuelan Equine Encephalitis (VEE) alphavirus RNA replicon particles. In yet more specific embodiments, all of VEE alphavirus RNA replicon particles in the immunogenic compositions are TC-83 VEE alphavirus RNA replicon particles.

In additional embodiments, alphavirus RNA replicon particles can encode protein antigens (or antigenic fragments thereof) that originate from other feline pathogens. In particular embodiments of this type, the protein antigen originates from a feline pneumovirus (FPN). In still other embodiments, the protein antigen originates from feline parvovirus (FPV). In yet other embodiments, the protein antigen originates from feline infectious peritonitis virus (FIPV). In yet other embodiments, the protein antigen originates from feline immunodeficiency virus. In still other embodiments, the protein antigen originates from borna disease virus (BDV). In yet other embodiments, the protein antigen originates from feline influenza virus. In still other embodiments, the protein antigen originates from feline coronavirus (FCoV).

The present invention further provides immunogenic compositions and/or vaccines (multivalent vaccines) that include the alphavirus RNA replicon particles of the present invention together with one or more modified live (e.g., attenuated) feline pathogens of the present invention, together with a killed feline pathogen. In particular embodiments, the immunogenic compositions can further comprise a killed *Chlamydophila felis*, and/or killed FVR, and/or killed F9-like FCV, and/or killed VS-FCV, and/or killed FeLV, and/or killed FPLV. In certain embodiments, vaccines comprise an immunologically effective amount of one or more of these immunogenic compositions.

The present invention further comprises vaccines and multivalent vaccines that comprise the immunogenic compositions of the present invention. In particular embodiments, the multivalent vaccines are nonadjuvanted vaccines. In certain embodiments, the vaccine aids in the prevention of disease due to FCV, and/or FeLV, and/or FVR, and/or FPLV, and/or rabies virus, and/or *Chlamydophila felis*. In related embodiments, antibodies are induced in a feline subject when the feline is immunized with the vaccine. The present invention further includes all of the alphavirus RNA replicon particles and the naked DNA vectors of the present invention.

The present invention also provides methods of immunizing a feline against a feline pathogen, e.g., FCV, comprising administering to the feline an immunologically effective amount of a vaccine or multivalent vaccine of the present invention. In particular embodiments the vaccine is administered via intramuscular injection. In alternative embodiments the vaccine is administered via subcutaneous injection. In other embodiments the vaccine is administered via intravenous injection. In still other embodiments the vaccine is administered via intradermal injection. In yet other embodiments the vaccine is administered via transdermal injection. In still other embodiments the vaccine is administered via oral administration. In yet other embodiments the vaccine is administered via intranasal administration. In specific embodiments, the feline is a domestic cat.

The vaccines and multivalent vaccines of the present invention can be administered as a primer vaccine and/or as a booster vaccine. In specific embodiments, a vaccine of the present invention is administered as a one shot vaccine (one dose), without requiring subsequent administrations. In certain embodiments, in the case of the administration of both a primer vaccine and a booster vaccine, the primer vaccine and the booster vaccine can be administered by the identical route. In certain embodiments of this type, the primer vaccine and the booster vaccine are both administered by subcutaneous injection. In alternative embodiments, in the case of the administration of both a primer vaccine and a booster vaccine, the administration of the primer vaccine can be performed by one route and the booster vaccine by another route. In certain embodiments of this type, the primer vaccine can be administered by subcutaneous injection and the booster vaccine can be administered orally.

The invention further provides for a method of immunizing a feline against FCV comprising injecting the feline with an immunologically effective amount of the above described inventive vaccines. In particular embodiments, the vaccines can include from about $1\times10^4$ to about $1\times10^{10}$ RPs or higher, for example. In more particular embodiments, the vaccines can include from about $1\times10^5$ to about $1\times10^9$ RPs. In even more particular embodiments the vaccines can include from about $1\times10^6$ to about $1\times10^8$ RPs. In particular embodiments, the feline is a domestic cat.

In particular embodiments the vaccines of the present invention are administered in 0.05 mL to 3 mL doses. In more particular embodiments the dose administered is 0.1 mL to 2 mLs. In still more particular embodiments the dose administered is 0.2 mL to 1.5 mLs. In even more particular embodiments the dose administered is 0.3 to 1.0 mLs. In still more particular embodiments the dose administered is 0.4 mL to 0.8 mLs.

These and other aspects of the present invention will be better appreciated by reference to the following Detailed Description.

DETAILED DESCRIPTION OF THE INVENTION

The present invention provides safe and efficacious multivalent vaccines. In particular embodiments the vaccine is nonadjuvanted. In this aspect of the invention, the vaccines do not induce feline injection-site sarcomas, yet still aid in the protection of the vaccinates from disease caused by infections by feline calicivirus (FCV) and/or feline leukemia virus (FeLV), and infections by feline viral rhinotracheitis virus (FVR), and/or feline panleukopenia virus (FPLV), and/or live *Chlamydophila felis*.

Despite the known enhancement of the innate immune system by alphavirus RNA replicon particles, the multivalent vaccines of the present invention, which comprise both alphavirus RNA replicon particles and modified live viruses, are unexpectedly safe and efficacious, without the alphavirus RNA replicon particles significantly interfering with the immunological effect of the modified live viruses. Indeed, alphavirus RNA replicon particles, and in particular Venezuelan Equine Encephalitis (VEE) alphavirus RNA replicon particles, have previously been shown to catalyze a systemic antiviral state and protect against lethal virus challenge [Konopka et al., *J. Virol.,* 83 (29):12432-12442 (2009)]. Moreover, VEE alphavirus RNA replicon particles have been reported to induce rapid protection against foot-and-mouth disease virus [Segundo et al., *J. Virol.,* 87 (10): 5447-5460 (2013)]. Therefore, it would have been anticipated that vaccines comprising both alphavirus RNA replicon particles and modified live viruses would lead to a substantial inhibition of the immunological effect of the modified live viruses. However, the enhancement of the innate immune response due to the presence of the alphavirus RNA replicon particles surprisingly proved not to be detrimental to the immune response induced by the accompanying modified live viruses.

Accordingly, in a particular aspect, the present invention provides vaccines that comprise alphavirus RNA replicon particles that encode an FCV capsid protein or antigenic fragment thereof and/or an FeLV gp85 or antigentic fragment thereof, along with a modified live feline FVR, and/or a modified live FPLV, and/or a modified live *Chlamydophila felis*. In yet another aspect of the present invention, the vaccines comprise naked DNA vectors that encode an FCV capsid protein or antigenic fragment thereof and/or an FeLV gp85 or antigentic fragment thereof, along with a modified live feline FVR, and/or a modified live FPLV, and/or a modified live *Chlamydophila felis*.

The vaccines of the present invention can be administered to a feline in the absence of an adjuvant and still effectively aid in the protection of the vaccinated feline against FCV.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "alphavirus RNA replicon particle" includes reference to a plurality of such alphavirus RNA replicon particles, unless otherwise indicated.

As used herein the term "approximately" is used interchangeably with the term "about" and signifies that a value is within fifty percent of the indicated value i.e., a composition containing "approximately" $1\times10^8$ alphavirus RNA replicon particles per milliliter contains from $0.5\times10^8$ to $1.5\times10^8$ alphavirus RNA replicon particles per milliliter.

As used herein, the term "feline" refers to any member of the Felidae family. Domestic cats, pure-bred and/or mongrel companion cats, and wild or feral cats are all felines.

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in structural proteins, e.g., the capsid and glycoproteins, which also are derived from an alphavirus, e.g., as described by Pushko et al., [*Virology* 239(2):389-401 (1997)]. An RP cannot propagate in cell cultures or animal hosts (without a helper plasmid or analogous component), because the replicon does not encode the alphavirus structural components (e.g., capsid and glycoproteins).

The terms "FCV F9-Like" and "F9-Like FCV" are used interchangeably with each other and with the term "classical FCV" and as used herein is an FCV that can be characterized as an older and formerly, universal vaccine strain of FCV, for which the FCV F9 strain is considered a typical representative. In direct contrast, the FCV termed virulent systemic "VS-FCV" or as used herein interchangeably "(VS) FCV", is a newer class of FCV, which is unusually virulent, and cannot be neutralized by antibodies from the FCV F9-Like strains [see, U.S. Pat. No. 7,449,323; Radford et al., 38(2) Vet res. 319-335 (2007)].

The terms "originate from", "originates from" and "originating from" are used interchangeably with respect to a given protein antigen and the pathogen or strain of that pathogen that naturally encodes it, and as used herein signify that the unmodified and/or truncated amino acid sequence of that given protein antigen is encoded by that pathogen or strain of that pathogen. The coding sequence, within a nucleic acid construct of the present invention for a protein antigen originating from a pathogen, may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

As used herein, the terms "protecting", or "providing protection to", or "eliciting protective immunity to", "aids in prevention of disease", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, a "vaccine" is a composition that is suitable for application to an animal, e.g., feline (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. Accordingly, "adjuvants" are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates. The American Association of Feline Practitioners *Feline Vaccination Guidelines*, for example, suggest the use of nonadjuvanted FeLV vaccines [AAFP *Feline Advisory Panel,* 15: 785-808 (2013)].

As used herein, a "nonadjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., feline.

Parenteral administration" includes subcutaneous injections, submucosal injections, intravenous injections, intramuscular injections, intradermal injections, and infusion.

As used herein the term "antigenic fragment" in regard to a particular protein (e.g., a protein antigen) is a fragment of that protein that is antigenic, i.e., capable of specifically interacting with an antigen recognition molecule of the immune system, such as an immunoglobulin (antibody) or T cell antigen receptor. For example, an antigenic fragment of an FCV capsid protein is a fragment of the capsid protein that is antigenic. Preferably, an antigenic fragment of the present invention is immune-dominant for antibody and/or T cell receptor recognition. In particular embodiments, an antigenic fragment with respect to a given protein antigen is a fragment of that protein that retains at least 25% of the antigenicity of the full length protein. In preferred embodiments, an antigenic fragment retains at least 50% of the antigenicity of the full length protein. In more preferred embodiments, an antigenic fragment retains at least 75% of the antigenicity of the full length protein. Antigenic fragments can be as small as 20 amino acids or at the other extreme, be large fragments that are missing as little as a single amino acid from the full-length protein. In particular embodiments, the antigenic fragment comprises 25 to 150 amino acid residues. In other embodiments, the antigenic fragment comprises 50 to 250 amino acid residues. For example, for FeLV, the FeLV gp45 glycoprotein and the FeLV gp70 glycoprotein are antigenic fragments of the FeLV gp85 glycoprotein, whereas, for FCV, one antigenic fragment of an FCV capsid protein comprises region E of the ORF2.

As used herein, one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, N.C. 27519), Vector NTI (Informax, Inc. Mo.), Oxford Molecular Group PLC (1996) and the Clustal W algorithm with the alignment default parameters and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein, the term "inactivated" microorganism is used interchangeably with the term "killed" microorganism. For the purposes of this invention, an "inactivated" microorganism is an organism which is capable of eliciting an immune response in an animal, but is not capable of infecting the animal. An antigen of the present invention (e.g., an inactivated feline calicivirus) may be inactivated by an agent selected from the group consisting of binary ethyleneimine, formalin, beta-propiolactone, thimerosal, or heat. In a particular embodiment, inactivated feline calicivirus isolates combined with an RP of the present invention are inactivated by binary ethyleneimine.

The alphavirus RNA replicon particles of the present invention may be lyophilized and rehydrated with a sterile water diluent. On the other hand, when the alphavirus RNA replicon particles are stored separately, but intended to be mixed with other vaccine components prior to administration, the alphavirus RNA replicon particles can be stored in the stabilizing solution of those components, e.g., a high sucrose solution.

A vaccine of the present invention can be readily administered by any standard route including intravenous, intramuscular, subcutaneous, oral, intranasal, intradermal, and/or intraperitoneal vaccination. The skilled artisan will appreciate that the vaccine composition is preferably formulated appropriately for each type of recipient animal and route of administration.

Thus, the present invention also provides methods of immunizing a feline against feline pathogens. One such method comprises injecting a feline with an immunologically effective amount of a vaccine of the present invention, so that the feline produces appropriate anti-pathogen antibodies.

Multivalent Vaccines

Accordingly, the present invention provides multivalent vaccines comprising at least one modified live feline pathogen and one or more alphavirus RNA replicon particles. For example, the coding sequence of a protein antigen or antigenic fragment thereof, or combination of such coding sequences of protein antigens useful in a feline vaccine can be added to an alphavirus RNA replicon particle (RP) or combined in the same RP as one that encodes e.g., an FCV capsid protein and/or the FeLV glycoprotein (gp85) in the multivalent vaccine.

In specific embodiments, vaccines comprise at least one modified live feline pathogen and an alphavirus RNA replicon particle that encodes an FCV F9-Like capsid protein or an antigenic fragment thereof, and/or a VS-FCV capsid protein or an antigenic fragment thereof, with another alphavirus RNA replicon particle that encodes an FeLV gp85 or an antigenic fragment thereof. In other embodiments, vaccines comprise at least one modified live feline pathogen and one alphavirus RNA replicon particle that encodes a VS-FCV capsid protein or an antigenic fragment thereof, another alphavirus RNA replicon particle that encodes an FeLV gp85 or an antigenic fragment thereof, and still a third alphavirus RNA replicon particle that encodes an FCV F9-Like capsid protein or an antigenic fragment thereof. In yet other embodiments, vaccines comprise at least one modified live feline pathogen and an alphavirus RNA replicon particle that encodes an FCV F9-Like capsid protein or an antigenic fragment thereof, a VS-FCV capsid protein or an antigenic fragment thereof, and an FeLV gp85 or an antigenic fragment thereof.

Examples of pathogens that one or more of such protein antigens can originate from include feline viral rhinotracheitis Virus (FVR), feline leukemia virus (FeLV), feline panleukopenia Virus (FPL) feline herpesvirus (FHV), other FCV strains, feline parvovirus (FPV), feline infectious peritonitis virus (FIPV), feline immunodeficiency virus, borna disease virus (BDV), rabies virus, feline influenza virus, canine influenza virus, avian influenza, canine pneumovirus, feline pneumovirus, *Chlamydophila felis* (FKA *Chlamydophila psittaci*), *Bordetella bronchiseptica*, and *Bartonella* spp. (e.g., *B. henselae*). In particular embodiments, a coding sequence for a capsid protein or analogous protein from one or more of these feline or canine pathogens can be inserted into the same RP as the FCV antigen. Alternatively, or in combination therewith, a coding sequence for a capsid protein or analogous protein from one or more of these feline or canine pathogens can be inserted into one or more other RPs, which can be combined in a vaccine with an RP that encodes the FCV F9-Like capsid protein or an antigenic fragment thereof and/or the VS-FCV capsid protein or an antigenic fragment thereof.

Accordingly, the present invention provides vaccines comprising one or more alphavirus RNA replicon particles (RP) of the present invention [e.g., a VS-FCV capsid protein or an antigenic fragment thereof] along with one or more modified live (attenuated) virus isolates, e.g., a live attenuated older vaccine strain of FCV, such as a live attenuated FCV F9, and/or a live attenuated feline herpesvirus and/or a live attenuated feline parvovirus and/or a live, attenuated feline leukemia virus, and/or a live, attenuated feline infectious peritonitis virus and/or a live, attenuated feline immunodeficiency virus and/or a live, attenuated borna disease virus and/or a live, attenuated rabies virus, and/or a live, attenuated feline influenza virus and/or a live, attenuated canine influenza virus, and/or a live, attenuated avian influenza, and/or a live, attenuated canine pneumovirus, and/or a live, attenuated feline pneumovirus. In addition, a live, attenuated *Chlamydophila felis*, and/or a live, attenuated *Bordetella bronchiseptica* and/or a live, attenuated *Bartonella* spp. (e.g., *B. henselae*) also can be included in such multivalent vaccines.

Furthermore, the vaccines of the present invention comprising one or more alphavirus RNA replicon particles of the present invention [e.g., encoding a VS-FCV capsid protein or an antigenic fragment thereof] with one or more modified live, virus isolates, further can comprise one or more killed virus isolates such as a killed FCV strain, and/or a killed feline herpesvirus and/or a killed feline parvovirus and/or a killed feline leukemia virus, and/or a killed feline infectious peritonitis virus and/or a killed feline immunodeficiency virus and/or a killed borna disease virus and/or a killed rabies virus, and/or a killed feline influenza virus and/or a killed canine influenza virus, and/or a killed avian influenza virus, and/or a killed canine pneumovirus, and/or a killed feline pneumovirus. In addition, bacterins of *Chlamydophila felis*, and/or *Bordetella bronchiseptica* and/or *Bartonella* spp. (e.g., *B. henselae*) can also be included in such multivalent vaccines.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

SEQUENCE TABLE

| SEQ ID NO: | Description | Type |
|---|---|---|
| 1 | Feline Calicivirus (VS-FCV) | nucleic acid DNA |
| 2 | Feline Calicivirus (VS-FCV) | amino acid |
| 3 | Feline Calicivirus (F9-like) | nucleic acid DNA |
| 4 | Feline Calicivirus (F9-like) | amino acid |
| 5 | FeLV viral glycoprotein (gp85) | nucleic acid DNA |
| 6 | FeLV viral glycoprotein (gp85) | amino acid |
| 7 | FeLV viral glycoprotein (gp70) | nucleic acid DNA |
| 8 | FeLV viral glycoprotein (gp70) | amino acid |
| 9 | Rabies virus Glycoprotein | nucleic acid DNA |
| 10 | Rabies virus Glycoprotein | amino acid |
| 11 | GGCGCGCCGCACC | nucleic acid |
| 12 | Feline Calicivirus (VS-FCV) | nucleic acid RNA |
| 13 | Feline Calicivirus (F9-like) | nucleic acid RNA |
| 14 | FeLV viral glycoprotein (gp85) | nucleic acid RNA |
| 15 | FeLV viral glycoprotein (gp70) | nucleic acid RNA |
| 16 | Rabies virus Glycoprotein | nucleic acid RNA |
| | TTAATTAA | nucleic acid |

SEQUENCES

Feline Calicivirus capsid (VS-FCV)

SEQ ID NO: 1 atggctgacgacggatctgtgaccaccccagaacaaggaacaatggtcggaggagtgatt
gccgaacccagcgctcagatgtcaactgcggcggacatggcctccggaaagtcggtggac
tccgagtgggaagccttcttctcgttccacacgtccgtgaactggagcacctccgaaacc
caaggaaagatcctcttcaagcagtccctgggtcccctgctgaacccgtacctggagcac
atcagcaagctgtacgtcgcttggagcgggtcgatcgaagtgcgattttccatctcggga
agcggcgtgttcggtggtaaactggccgccatcgtcgtgccgcctggtgtcgaccctgtc
cagtcaacctccatgctgcagtacccgcacgtcctgttcgacgcaagacaagtggagcca
gtgatcttctccatcccggacctccgcaacagcctgtatcacttgatgtccgataccgat
accacttccctcgtgatcatggtgtacaacgatctgatcaacccgtacgccaatgactcc
aacagctcgggttgcatcgtgaccgtcgaaacgaagcctggcatcgatttcaagtttcat
ctgctgaaaccgcccggatccatgcttactcacgggtccatcccttccgatctgatcccc
aagagctcctccctgtggattgggaaccgccactggaccgatattaccgatttcgtgatt
cggcctttcgtgttccaagccaaccggcacttcgacttcaaccaggagactgccggctgg
tcaactccacggttccgcccattggccgtgactgtgtcgcagtcaaagggagccaagctc
gggaacggcatcgccaccgactacattgtgcctggaatccccgacggatggcctgatact
accatccccaccaagctgacccctaccggagattacgccatcacctcctccgacggcaat
gatattgaaaccaagctggaatacgagaacgcggacgtgattaagaacaacaccaacttc
cgctccatgtatatctgcggaagcctccagagggcttggggcgacaagaagatcagcaac
accgggttcatcactaccggagtgatttctgacaactccatcagcccttcgaacacaatt
gaccagtccaagatcgtggtgtaccaggacaaccatgtcaattcggaggtccagactagc
gacatcactcttgccatcctgggctacaccggaattggagaagaggccataggcgccaac
cgggactccgtcgtgagaatttccgtgcttccggaaactggagcaaggggcggaaatcac
cccatcttctacaaaaattccatgaagctgggctacgtgatctcctccattgacgtgttc
aactcccaaatcctccacacctcgcgccagctgtcactgaacaactacttgttgcccccct
gactccttcgcggtgtaccggattattgacagcaacggatcatggttcgacattgggatt
gacagcgatgggttttcattcgtgggcgtgtcgtcatttccaaagctggagtttccgctg
tccgcctcatacatgggcatccagctcgcaaagatccggctggcgtccaacatccggtca
tccatgactaagctgtga Feline Calicivirus capsid (VS-FCV)

SEQ ID NO: 2

MADDGSVTTPEQGTMVGGVIAEPSAQMSTAADMASGKSVDSEWEAFFSFHTSVNWSTSET
QGKILFKQSLGPLLNPYLEHISKLYVAWSGSIEVRFSISGSGVFGGKLAAIVVPPGVDPV
QST MLQYPHVLFDARQVEPVIFSIPDLRNSLYHLMSDTDTTSLVIMVYNDLINPYANDS
NSSGCIVTVETKPGIDFKFHLLKPPGSMLTHGSIPSDLIPKSSSLWIGNRHWTDITDFVI
RPFVFQANRHFDFNQETAGWSTPRFRPLAVTVSQSKGAKLGNGIATDYIVPGIPDGWPDT
TIPTKLTPTGDYAITSSDGNDIETKLEYENADVIKNNTNFRSMYICGSLQRAWGDKKISN
TGFITTGVISDNSISPSNTIDQSKIVVYQDNHVNSEVQTSDITLAILGYTGIGEEAIGAN

-continued

RDSVVRISVLPETGARGGNHPIFYKNSMKLGYVISSIDVFNSQILHTSRQLSLNNYLLPP

DSFAVYRIIDSNGSWFDIGIDSDGFSFVGVSSFPKLEFPLSASYMGIQLAKIRLASNIRS

SMTKL

Feline Calicivirus (VS-FCV) capsid (SEQ ID NO: 12)

auggcugacgacggaucugugaccaccccagaacaaggaacaauggucggaggagugauu gccgaacccagcgcucagaugucaacugcggcggacauggccuccggaaagucgguggac uccgagugggaagccuucuucucguuccacacguccgugaacuggagcaccuccgaaacc caaggaaagauccucuucaagcagucccugggucccugcugaacccguaccuggagcac aucagcaagcuguacgucgcuuggagcgggucgaucgaagugcgauuuuccaucucggga agcggcguguucgguggauaaacuggccgccaucgucgugccgccuggugucgacccuguc cagucaaccuccaugcugcaguacccgcacguccuguucgacgcaagacaaguggagcca gugaucuucuccaucccggaccuccgcaacagccuguaucacuugauguccgauaccgau accacuucccucgugaucaugguguacaacgaucugaucaacccguacgccaaugacucc aacagcucggguugcaucgugaccgucgaaacgaagccuggcaucgauuucaaguuucau cugcugaaaccgcccggauccaugcuuacucacggguccaucccuuccgaucugaucccc aagagcuccucccuguggauugggaaccgccacuggaccgauauuaccgauuucgugauu cggccuuucguguuccaagccaaccggcacuucgacuucaaccaggagacugccggcugg ucaacuccacgguuccgcccauuggccgugacugugucgcagucaaagggagccaagcuc gggaacggcaucgccaccgacuacauugugccuggaauccccgacggauggccugauacu accauccccaccaagcugaccccuaccggagauuacgccaucaccuccuccgacggcaau gauauugaaaccaagcuggaauacgagaacgcggacgugauuaagaacaacaccaacuuc cgcuccauguauaucugcggaagccuccagagggcuuggggcgacaagaagaucagcaac accggguucaucacuaccggagugauuucugacaacuccaucagcccuucgaacacaauu gaccaguccaagaucgugguguaccaggacaaccaugucaauucggagguccagacuagc gacaucacucuugccauccugggcuacaccggaauuggagaagaggccauaggcgccaac cgggacuccgucgugagaauuuccgugcuuccggaaacuggagcaaggggcggaaaucac cccaucuucuacaaaaauuccaugaagcugggcuacgugaucuccuccauugacguguuc aacucccaaauccuccacaccucgcgccagcugucacugaacaacuacuuguugccccu gacuccuucgcgguguaccggauuauugacagcaacggaucaugguucgacauugggauu gacagcgauggguuuucauucgugggcgugucgucauuuccaaagcuggaguuuccgcug uccgccucauacaugggcauccagcucgcaaagauccggcuggcguccaacauccgguca uccaugacuaagcuguga Feline Calicivirus (F9-like) capsid (SEQ ID NO: 3)

atgactgccccggaacaaggaacgatggtcggaggagtgattgcagaaccgtcagcacag atgtccaccgctgccgacatggccactggaaagagcgtggactccgaatgggaagccttc ttctccttccacacttcggtcaactggtcgactagcgaaacccaggggaagattttgttc aagcaatccctcggccctctgctgaacccctacctggagcatctggccaagctgtacgtg gcatggtcgggcagcatcgaagtgcgctttagcatttccggctccggagtgttcgggga aagcttgctgccattgtcgtgccgccaggagtggacccggtgcagtccacttctatgctc caatacccgcatgtcctgttcgacgccagacaggtggagcctgtgatcttttgcctgccg gatctcaggtccaccctgtatcacctcatgtccgacaccgacaccacctcgctcgtgatc -continued atggtgtacaacgacctgatcaacccctacgctaacgacgccaacagctcaggttgcatt gtgactgtcgaaaccaagccaggccctgacttcaagtttcatttgctgaagccgcccggt tccatgctgacccacggctcgatcccatccgacctgatccccaagacgagctccctgtgg atcggaaaccgctactggtccgatattaccgacttcgtgatcagaccattcgtgttccaa gccaaccgccatttcgacttcaaccaggaaaccgcaggatggtcgacccctcgattccgc ccgatttcagtgaccatcaccgaacagaacggcgcgaagctgggaattggcgtggcgacc gactacatcgtgccgggaatcccggatggatggcctgatacgaccattcccggggagctg atccctgccggggactacgccatcaccaacggtactggaaacgacatcaccactgccacc ggttacgacaccgccgacatcataaagaacaacaccaacttcagaggaatgtacatttgc ggctccctgcaacgcgcttggggtgacaaaaagatctcgaacactgccttcatcacaaca gcgactctggacggcgataacaacaacaagatcaatccttgtaataccatcgaccagtcc aaaatcgtggtgttccaggataaccacgtgggaaagaaggcgcagacctccgacgacact ctggcgctgcttggctacaccgggatcggcgagcaggccattggaagcgatcgggatcgg gtcgtgcggatctccaccctccccgagactggagcaaggggaggcaaccaccccatcttt tacaaaaacagcattaagctcggatacgtcatccgctccatcgatgtgttcaactctcaa atcctgcacacttcgcggcagctgtccctgaaccactacctcttgccgcccgactccttc gccgtctaccggatcattgattcgaacgggagctggttcgacatcggcattgatagcgat ggcttctcgtttgtgggcgtgtcgggcttcgggaagctggagttcccactgagcgcctca tacatgggtatccagctggccaagatcaggctggcctccaacatccgctcacctatgact aagctgtga Feline Calicivirus (F9-like) capsid (SEQ ID NO: 4)

MTAPEQGTMVGGVIAEPSAQMSTAADMATGKSVDSEWEAFFSFHTSVNWSTSETQGKILF

KQSLGPLLNPYLEHLAKLYVAWSGSIEVRFSISGSGVFGGKLAAIVVPPGVDPVQSTSML

QYPHVLFDARQVEPVIFCLPDLRSTLYHLMSDTDTTSLVIMVYNDLINPYANDANSSGCI

VTVETKPGPDFKFHLLKPPGSMLTHGSIPSDLIPKTSSLWIGNRYWSDITDFVIRPFVFQ

ANRHFDFNQETAGWSTPRFRPISVTITEQNGAKLGIGVATDYIVPGIPDGWPDTTIPGEL

IPAGDYAITNGTGNDITTATGYDTADIIKNNTNFRGMYICGSLQRAWGDKKISNTAFITT

ATLDGDNNNKINPCNTIDQSKIVVFQDNHVGKKAQTSDDTLALLGYTGIGEQAIGSDRDR

VVRISTLPETGARGGNHPIFYKNSIKLGYVIRSIDVFNSQILHTSRQLSLNHYLLPPDSF

AVYRIIDSNGSWFDIGIDSDGFSFVGVSGFGKLEFPLSASYMGIQLAKIRLASNIRSPMT

KL

Feline Calicivirus (F9-like) capsid (SEQ ID NO: 13)

augacugccccggaacaaggaacgauggucggaggagugauugcagaaccgucagcacag auguccaccgcugccgacauggccacuggaaagagcguggacuccgaaugggaagccuuc uucuccuuccacacuucggucaacuggucgacuagcgaaacccaggggaagauuuuguuc aagcaaucccucggcccucugcugaaccccuaccuggagcaucuggccaagcuguacgug gcauggucgggcagcaucgaagugcgcuuuagcauuuccggcuccggaguguucgggga aagcuugcugccauugucgugccgccaggaguggacccggugcaguccacuucuaugcuc caauacccgcauguccuguucgacgccagacagguggagccugugaucuuuugccugccg gaucucagguccacccuguaucaccucauguccgacaccgacaccaccucgcucgugauc -continued auggguguacaacgaccugaucaaccccuacgcuaacgacgccaacagcucagguugcauu gugacugucgaaaccaagccaggcccugacuucaaguuucauuugcugaagccgcccggu uccaugcugacccacggcucgaucccauccgaccugauccccaagacgagcucccugugg aucggaaaccgcuacugguccgauauuaccgacuucgugaucagaccauucguguuccaa gccaaccgccauuucgacuucaaccaggaaaccgcaggauggucgaccccucgauuccgc ccgauuucagugaccaucaccgaacagaacggcgcgaagcugggaauuggcguggcgacc gacuacaucgugccgggaaucccggauggauggccugauacgaccauucccggggagcug aucccugccggggacuacgccaucaccaacgguacuggaaacgacaucaccacugccacc gguuacgacaccgccgacaucauaaagaacaacaccaacuucagaggaauguacauuugc ggcucccugcaacgcgcuuggggugacaaaaagaucucgaacacugccuucaucacaaca gcgacucuggacggcgauaacaacaacaagaucaauccuuguaauaccaucgaccagucc aaaaucgugguguuccaggauaaccacgugggaaagaaggcgcagaccuccgacgacacu cuggcgcugcuuggcuacaccgggaucggcgagcaggccauuggaagcgaucgggaucgg gucgugcggaucuccacccuccccgagacuggagcaaggggaggcaaccaccccaucuuu uacaaaaacagcauuaagcucggauacgucauccgcuccaucgauguguucaacucucaa auccugcacacuucgcggcagcugucccugaaccacuaccucuugccgcccgacuccuuc gccgucuaccggaucauugauucgaacgggagcugguucgacaucggcauugauagcgau ggcuucucguuugugggcgugucgggcuucgggaagcuggaguucccacugagcgccuca uacauggguauccagcuggccaagaucaggcuggccuccaacauccgcucaccuaugacu aagcuguga Feline Leukemia Virus envelope glycoprotein (gp85)

SEQ ID NO: 5 atggagtcaccaacacaccctaaaccttctaaagacaaaaccctctcgtggaatctcgccttccttgt gggcatcctgttcacaatcgacatcggcatggccaacccttcgccgcatcagatctacaatgtgacat gggtcattactaatgtgcagacaaacacccaggcaaatgctacttctatgcttggtactctgactgat gcttatccaaccctgcacgtcgacctttgcgatctcgtcggtgacacatgggagcccatcgtgctgaa tccaactaatgtcaaacatggtgccaggtattcttctagcaaatacgggtgtaagaccactgatcgga agaaacagcaacaaacctacccattctacgtgtgcccgggtcacgcaccgtccctgggtccgaaggga acacattgtgggggagcccaagacggtttttgcgctgcttggggttgtgaaacaaccggagaagcctg gtggaagcctacctcatcttgggactacattactgtgaaaagaggctctagccaggataacagctgcg aaggaaagtgtaatcccctggtgcttcaattcacccagaaaggccggcaggcatcatgggatggaccg aaaatgtggggacttagactctatcgcaccggatacgaccccatcgctctgtttactgtgtcacgcca agtctccaccattactccgccacaggccatggggccgaatctggtcctccccgatcagaagccaccct cacggcaaagtcaaaccggctcaaaagtggccacccaacggccccagacaaatgagtccgcacctagg tcagtggcacctacaacaatgggtccaaagcggatcggaaccggagacaggctcattaacctcgtgca agggacttatctggcccttaacgctactgaccccaacaagaccaaggattgctggctctgccttgtga gcagacctccttactatgaggggatcgccattctcggaaactactcaaatcagaccaacccccctccg tcgtgtctgagcacccccccagcacaagcttactatttcagaagtcagtggacagggaatgtgcatcgg aaccgtgccaaagactcatcaagccctttgcaacaaaactcaacaagggcacactggagctcattatc tcgccgcacctaacgggacctactgggcttgcaatactggattgaccccgtgtatctctatggccgtg ctgaattggacttccgacttctgcgtgcttattgagctttggcctagagtgacataccatcagcctga gtacgtctatacccatttcgccaaggcagtcagattccggcgggagcctatctccctgactgtggcct -continued tgatgctcggtggactgacagtgggaggaattgcagctggagtcggaactggaaccaaggccctgctc gaaactgctcagttccggcagctgcagatggccatgcacactgacatccaggctctggaggaatcaat ttcagcccttgagaaaagcttgacctcgctgtctgaagtggtcctccaaaacaggcgcggtttggaca tcctgttccttcaagagggtggtctgtgcgccgctctcaaggaggaatgctgtttctacgctgaccat accgggctggtgcgcgataacatggcaaagctgcgggaacgcttgaaacagaggcagcaactgttcga ctctcagcagggatggttcgagggctggtttaacaagagcccatggtttaccactctgatctcttcaa tcatgggtccactgctcatcctgcttctgattcttctcttcggaccgtgtattctcaacaggctggtg cagtttgtcaaggacagaatctcggtggtccaggccctgattcttactcagcagtatcagcagattaa gcagtacgaccccgatcggccttga Feline Leukemia Virus envelope glycoprotein (gp85)

SEQ ID NO: 6

MESPTHPKPSKDKTLSWNLAFLVGILFTIDIGMANPSPHQIYNVTWVITNVQTNTQANAT

SMLGTLTDAYPTLHVDLCDLVGDTWEPIVLNPTNVKHGARYSSSKYGCKTTDRKKQQQTY

PFYVCPGHAPSLGPKGTHCGGAQDGFCAAWGCETTGEAWWKPTSSWDYITVKRGSSQDNS

CEGKCNPLVLQFTQKGRQASWDGPKMWGLRLYRTGYDPIALFTVSRQVSTITPPQAMGPN

LVLPDQKPPSRQSQTGSKVATQRPQTNESAPRSVAPTTMGPKRIGTGDRLINLVQGTYLA

LNATDPNKTKDCWLCLVSRPPYYEGIAILGNYSNQTNPPPSCLSTPQHKLTISEVSGQGM

CIGTVPKTHQALCNKTQQGHTGAHYLAAPNGTYWACNTGLTPCISMAVLNWTSDFCVLIE

LWPRVTYHQPEYVYTHFAKAVRFRREPISLTVALMLGGLTVGGIAAGVGTGTKALLETAQ

FRQLQMAMHTDIQALEESISALEKSLTSLSEVVLQNRRGLDILFLQEGGLCAALKEECCF

YADHTGLVRDNMAKLRERLKQRQQLFDSQQGWFEGWFNKSPWFTTLISSIMGPLLILLLI

LLFGPCILNRLVQFVKDRISVVQALILTQQYQQIKQYDPDRP*

Feline Leukemia Virus envelope glycoprotein (gp85)

SEQ ID NO: 14 auggagucaccaacacacccuaaaccuucuaaagacaaaacccucucgugggaaucucgccuuccuugu gggcauccuguucacaaucgacaucggcauggccaacccuucgccgcaucagaucuacaaugugacau gggucauuacuaaugugcagacaaacacccaggcaaaugcuacuucuaugcuugguacucugacugau gcuuauccaacccugcacgucgaccuuugcgaucucgucggugacacaugggagcccaucgugcugaa uccaacuaaugucaaacauggugccagguauucuucuagcaaauacggguguaagaccacugaucgga agaaacagcaacaaaccuacccauucuacgugugcccgggucacgcaccgucccuggguccgaaggga acacauugugggggagcccaagacgguuuuugcgcugcuuggggguugugaaacaaccggagaagccug guggaagccuaccucaucuugggacuacauuacugugaaaagaggcucuagccaggauaacagcugcg aaggaaaguguaauccccuggugcuucaauucacccagaaaggccggcaggcaucaugggauggaccg aaaaugugggggacuuagacucuaucgcaccggauacgaccccaucgcucuguuuacugugucacgcca agucuccaccauuacuccgccacaggccauggggccgaaucugguccuccccgaucagaagccacccu cacggcaaagucaaaccggcucaaaaguggccacccaacggccccagacaaaugaguccgcaccuagg ucaguggcaccuacaacaaugggguccaaagcggaucggaaccggagacaggcucauuaaccucgugca agggacuuaucuggcccuuuaacgcuacugaccccaacaagaccaaggauugcuggcucugccuuguga gcagaccucccuuacuaugaggggaucgccauucucggaaacuacucaaaucagaccaaccccccuccg ucgugucugagcacccccagcacaagcuuacuauuucagaagucaguggacagggaaugugcaucgg aaccgugccaaagacucaucaagcccuuugcaacaaaacucaacaagggcacacuggagcucauuauc ucgccgcaccuaacgggaccuacugggcuugcaauacuggauugaccccguguaucucuauggccgug -continued cugaauuggacuuccgacuucugcgugcuuauugagcuuuggccuagagugacauaccaucagccuga guacgucuauacccauuucgccaaggcagucagauuccggcgggagccuaucucccugacuguggccu ugaugcucgguggacugacagugggaggaauugcagcuggagucggaacuggaaccaaggcccugcuc gaaacugcucaguuccggcagcugcagauggccaugcacacugacauccaggcucuggaggaaucaau uucagcccuugagaaaagcuugaccucgcugucugaagugguccuccaaaacaggcgcgguuuggaca uccuguuccuucaagagggguggucugugcgccgcucucaaggaggaaugcuguuucuacgcugaccau accgggcuggugcgcgauaacauggcaaagcugcgggaacgcuugaaacagaggcagcaacuguucga cucucagcagggaugguucgagggcugguuuaacaagagcccaugguuuaccacucugaucucuucaa ucaugggucacugcucauccugcuucugauucuucucuucggaccguguauucucaacaggcuggug caguuugucaaggacagaaucucgguggguccaggcccugauucuuacucagcaguaucagcagauuaa gcaguacgaccccgaucggccuuga Feline Leukemia Virus envelope glycoprotein (gp70)

SEQ ID NO: 7 aatcctagtccacaccaaatatataatgtaacttgggtaataaccaatgtacaaactaacacc caagctaacgccacctctatgttaggaaccttaaccgatgcctaccctaccctacatgttgac ttatgtgacctagtgggagacacctgggaacctatagtcctaaacccaaccaatgtaaaacac ggggcacgttactcctcctcaaaatatggatgtaaaactacagatagaaaaaaacagcaacag acatacccctttttacgtctgccccggacatgccccctcgttggggccaaagggaacacattgt ggaggggcacaagatgggttttgtgccgcatggggatgtgagaccaccggagaagcttggtgg aagcccacctcctcatgggactatatcacagtaaaaagagggagtagtcaggacaatagctgt gagggaaaatgcaacccccctggttttgcagttcacccagaagggaagacaagcctcttgggac ggacctaagatgtggggattgcgactataccgtacaggatatgaccctatcgctttattcacg gtgtcccggcaggtatcaaccattacgccgcctcaggcaatgggaccaaacctagtcttacct gatcaaaaacccccatcccgacaatctcaaacagggtccaaagtggcgacccagaggccccaa acgaatgaaagcgccccaaggtctgttgcccccaccaccatgggtcccaaacggattgggacc ggagataggttaataaatttagtacaagggacatacctagccttaaatgccaccgaccccaac aaaactaaagactgttggctctgcctggtttctcgaccaccctattacgaagggattgcaatc ttaggtaactacagcaaccaaacaaaccccccccatcctgcctatctactccgcaacacaaa ctaactatatctgaagtatcagggcaaggaatgtgcatagggactgttcctaaaacccaccag gctttgtgcaataagacacaacagggacatacaggggcgcactatctagccgcccccaacggc acctattgggcctgtaacactggactcaccccatgcatttccatggcggtgctcaattggacc tctgatttttgtgtcttaatcgaattatggcccagagtgacttaccatcaacccgaatatgtg tacacacattttgccaaagctgtcaggttccgaaga Feline Leukemia Virus envelope glycoprotein (gp70)

SEQ ID NO: 8

NPSPHQIYNVTWVITNVQTNTQANATSMLGTLTDAYPTLHVDLCDLVGDTWEPIVLNPTNVKHGARYSSS

KYGCKTTDRKKQQQTYPFYVCPGHAPSLGPKGTHCGGAQDGFCAAWGCETTGEAWWKPTSSWDYITVKRG

SSQDNSCEGKCNPLVLQFTQKGRQASWDGPKMWGLRLYRTGYDPIALFTVSRQVSTITPPQAMGPNLVLP

DQKPPSRQSQTGSKVATQRPQTNESAPRSVAPTTMGPKRIGTGDRLINLVQGTYLALNATDPNKTKDCWL

CLVSRPPYYEGIAILGNYSNQTNPPPSCLSTPQHKLTISEVSGQGMCIGTVPKTHQALCNKTQQGHTGAH

YLAAPNGTYWACNTGLTPCISMAVLNWTSDFCVLIELWPRVTYHQPEYVYTHFAKAVRFRR

-continued

Feline Leukemia Virus envelope glycoprotein (gp70)

SEQ ID NO: 15 aauccuaguccacaccaaauauauaaauguaacuuggguaaauaaccaauguacaaacuaacacc caagcuaacgccaccucuauguuaggaaccuuaaccgaugccuacccuacccuacauguugac uuaugugaccuagugggagacaccugggaaccuauaguccuaaacccaaccaauguaaaacac ggggcacguuacuccuccucaaaauauggauguaaaacuacagauagaaaaaaacagcaacag acauaccccuuuuacgucugccccggacaugccccucguuggggccaaagggaacacauugu ggaggggcacaagaugggguuuugugccgcauggggaugugagaccaccggagaagcuuggugg aagcccaccuccucaugggacuauaucacaguaaaaagagggaguagucaggacaauagcugu gagggaaaaugcaaccccccugguuuugcaguucacccagaagggaagacaagccucuugggac ggaccuaagauguggggauugcgacuauaccguacaggauaugacccuaucgcuuuauucacg gugucccggcagguaucaaccauuacgccgccucaggcaaugggaccaaaccuagucuuaccu gaucaaaaaccccccaucccgacaaucucaaacagggucccaaaguggcgacccagaggccccaa acgaaugaaagcgccccaaggucuguugcccccaccaccaugggucccaaacggauugggacc ggagauagguuaauaaaauuuaguacaagggacauaccuagccuuaaaugccaccgaccccaac aaaacuaaagacuguuggcucugccugguuucucgaccacccuauuacgaagggauugcaauc uuagguaacuacagcaaccaaacaaacccccccccauccugccuaucuacuccgcaacacaaa cuaacuauaucugaaguaucagggcaaggaaugugcauagggacuguuccuaaaacccaccag gcuuugugcaauaagacacaacagggacauacaggggcgcacuaucuagccgcccccaacggc accuauugggccuguaacacuggacucaccccaugcauuuccauggcggugcucaauuggacc ucugauuuuuguguucuuaaaucgaauuauggcccagagugacuuaccaucaacccgaauaugug uacacacauuuugccaaagcugucagguuccgaaga

RABIES VIRUS G (SEQ ID NO: 9)

atggtgccgcaggctctcctgtttgtccccccttctggtctttccattgtgttttgggaaattccctatctacacaattc cggacaagttgggaccctggagcccaattgacattcatcatctcagctgcccgaacaatttggtcgtggaggacgaagg atgcaccaacctgtcggggttctcctacatggaattgaaagtcggatacatcagtgccattaagatgaacgggttcact tgcacaggcgtcgtgactgaagctgagacatacactaacttcgtgggatatgtcactaccactttcaaaagaaagcatt tccgccctactcctgatgcttgtagggccgcatacaactggaagatggccggtgaccccagatatgaggaatcacttca caatccgtaccctgactaccactggcttcggactgtcaaaaccaccaaggagtcactcgtgatcattagtccaagtgtg gctgatcttgacccatacgaccggtcacttcactcacgggtgttcccgggggggaattgctctggtgtcgcagtgtcgt caacctactgctccacaaaccacgattacaccatttggatgccagaaaatcctcggcttggtatgtcatgtgacatttt caccaattctcggggggaagagggcttccaaagggtctgaaacttgcggctttgtcgatgagcggggcttgtataagtca cttaaaggtgcttgcaaactcaagctttgtggtgtcttgggattgagattgatggatggaacttgggtcgcaatgcaga cttctaacgaaaccaaatggtgccctcccggacagcttgtgaatttgcatgactttcgctctgacgaaattgagcatct tgtcgtcgaggagttggtcaagaagcgggaagagtgtctggatgctttggaatcaatcatgaccaccaagtcagtgtct ttcagacggctctcacatcttaggaaattggtgccaggttttggaaaagcatataccattttcaacaagaccccttatgg aagccgatgctcactacaagtctgtcaggacttggaatgagatcatcccgtctaaagggtgtcttagggtcggagggag atgtcatcctcatgtcaacggagtctttttcaatggtatcattcttggacctgacggaaatgtccttatccctgagatg caatcttccctcctccagcaacacatggaacttcttgtctcatcggtcatccccccttatgcacccccctggctgaccat caaccgtgttcaagaacggtgacgaggcagaggattttgtcgaggtccaccttcccgatgtgcatgaacggatctctgg tgtcgaccttggactccctaactggggaaagtatgtccttctgtcggcaggagccctgactgccttgatgttgattatc ttcctgatgacttgttggaggagagtcaatcggtcggagccaacacaacataatctcagaggaacaggaagggaggtgt -continued cagtcacaccccaaagcgggaagatcatttcgtcttgggagtcatacaagagcggaggtgaaaccggactgtga

RABIES VIRUS G (SEQ ID NO: 10)

MVPQALLFVPLLVFPLCFGKFPIYTIPDKLGPWSPIDIHHLSCPNNLVVEDEGCTNLSGF

SYMELKVGYISAIKMNGFTCTGVVTEAETYTNFVGYVTTTFKRKHFRPTPDACRAAYNWK

MAGDPRYEESLHNPYPDYHWLRTVKTTKESLVIISPSVADLDPYDRSLHSRVFPGGNCSG

VAVSSTYCSTNHDYTIWMPENPRLGMSCDIFTNSRGKRASKGSETCGFVDERGLYKSLKG

ACKLKLCGVLGLRLMDGTWVAMQTSNETKWCPPGQLVNLHDFRSDEIEHLVVEELVKKRE

ECLDALESIMTTKSVSFRRLSHLRKLVPGFGKAYTIFNKTLMEADAHYKSVRTWNEIIPS

KGCLRVGGRCHPHVNGVFFNGIILGPDGNVLIPEMQSSLLQQHMELLVSSVIPLMHPLAD

PSTVFKNGDEAEDFVEVHLPDVHERISGVDLGLPNWGKYVLLSAGALTALMLIIFLMTCW

RRVNRSEPTQHNLRGTGREVSVTPQSGKIISSWESYKSGGETGL*

RABIES VIRUS G (SEQ ID NO: 16)

auggugccgcaggcucuccuguuuguccccccuucuggucuuuccauuguguuuugggaaauucccuaucuacacaauuc cggacaaguugggacccuggagcccaauugacauucaucaucucagcugcccgaacaauuuggucguggaggacgaagg augcaccaaccugucgggguucuccuacauggaauugaaagucggauacaucagugccauuaagaugaacggguucacu ugcacaggcgucgugacugaagcugagacauacacuaacuucgugggauaugucacuaccacuuucaaaagaaagcauu uccgcccuacuccugaugcuuguagggccgcauacaacuggaagauggccggugaccccagauaugaggaaucacuuca caauccguacccugacuaccacuggcuucggacugucaaaaccaccaaggagucacucgugaucauuaguccaagugug gcugaucuugacccauacgaccggucacuucacucacggguguucccggggggggaauugcucuggugucgcagugucgu caaccuacugcuccacaaaccacgauuacaccauuuggaugccagaaaaucccucggcuugguaugucaugugacauuuu caccaauucucgggggaagagggcuucccaaagggucugaaacuugcggcuuugucgaugagcggggcuuguauaaguca cuuaaaggugcuugcaaacucaagcuuugugguguguuugggauugagauugauggauggaacuugggucgcaaugcaga cuucuaacgaaaccaaauggugcccucccggacagcuugugaauuugcaugacuuucgcucugacgaaauugagcaucu ugucgucgaggaguuggucaagaagcgggaagagugucuggaugcuuuggaaucaaucaugaccaccaagucagugucu uucagacggcucucacaucuuaggaaauuggugccagguuuuggaaaagcauauaccauuuucaacaagacccuuaugg aagccgaugcucacuacaagucugucaggacuuggaaugagaucaucccgucuaaagggugucuuagggucggagggag augucaucccucaugucaacggagucuuuuucaaugguaucauucuuggaccugacggaaauguccuuaucccugagaug caaucuucccucccuccagcaacacauggaacuucuugucucaucggucauccccccuuaugcacccccuggcugacccau caaccguguucaagaacggugacgaggcagaggauuuugucgagguccaccuucccgaugugcaugaacggaucucugg ugucgaccuuggacucccuaacuggggaaaguauguccuucugucggcaggagcccugacugccuugauguugauuauc uuccugaugacuuguuggaggagagucaaucggucggagccaacacaacauaaucucagaggaacaggaagggaggugu cagucacaccccaaagcgggaagaucauuucgucuugggagucauacaagagcggaggugaaaccggacuguga The following examples serve to provide further appreciation of the invention but are not meant in any way to restrict the effective scope of the invention.

EXAMPLES

Example 1

Incorporation of the Coding Sequences for FCV Capsid Proteins into the Alphavirus RNA Replicon Particles

Introduction

RNA viruses have been used as vector-vehicles for introducing vaccine antigens, which have been genetically engineered into their genomes. However, their use to date has been limited primarily to incorporating viral antigens into the RNA virus and then introducing the virus into a recipient host. The result is the induction of protective antibodies against the incorporated viral antigens. Alphavirus RNA replicon particles have been used to encode pathogenic antigens. Such alphavirus replicon platforms have been developed from several different alphaviruses, including Venezuelan equine encephalitis virus (VEE) [Pushko et al., Virology 239:389-401 (1997)], Sindbis (SIN) [Bredenbeek et al., *Journal of Virology* 67:6439-6446 (1993) the contents of which are hereby incorporated herein in their entireties], and Semliki Forest virus (SFV) [Liljestrom and Garoff, *Biotechnology* (NY) 9:1356-1361 (1991), the contents of which are hereby incorporated herein in their entireties]. Moreover, alphavirus RNA replicon particles are the basis for several USDA-licensed vaccines for swine and poultry. These include: Porcine Epidemic Diarrhea Vaccine, RNA Particle (Product Code 19U5.P1), Swine Influenza Vaccine, RNA (Product Code 19A5.D0), Avian Influenza Vaccine, RNA (Product Code 19O5.D0), and Prescription Product, RNA Particle (Product Code 9PP0.00).

Alphavirus RNA Replicon Particle Construction

RP-FCV:

Amino acid sequences for FCV capsid proteins were used to generate codon-optimized (feline codon usage) nucleotide sequences in silico. Optimized sequences were prepared as synthetic DNA by a commercial vendor (ATUM, Newark, Calif.). Accordingly, synthetic genes were designed based on the amino acid sequences of a VS-FCV capsid protein and an FCV F9-like capsid protein, respectively. The constructs encoded amino acid sequence [SEQ ID NO: 2] for the VS-FCV capsid protein, or [SEQ ID NO: 4] for the FCV F9-like capsid protein, were codon-optimized for feline, with flanking sequence appropriate for cloning into the alphavirus replicon plasmid.

The VEE replicon vectors designed to express FCV capsid proteins were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes Ascl and Pacl. A DNA plasmid containing the codon-optimized open reading frame nucleotide sequence of the FCV capsid genes, with 5' flanking sequence (5'-GGCGCGCCGCACC-3') [SEQ ID NO: 11] and 3' flanking sequence (5'-TTAATTAA-3'), were similarly digested with restriction enzymes Ascl and Pacl. The synthetic gene cassette was then ligated into the digested pVEK vector.

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference]. Briefly, pVHV replicon vector DNA and helper DNA plasmids were linearized with NotI restriction enzyme prior to in vitro transcription using MegaScript T7 RNA polymerase and cap analog (Promega, Madison, Wis.). Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to OptiPro® SFM cell culture media (Thermo Fisher, Waltham Mass.). Following overnight incubation, alphavirus RNA replicon particles were purified from the cells and media by passing the suspension through a ZetaPlus BioCap depth filter (3M, Maplewood, Minn.), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. Titer of functional RP was determined by immunofluorescence assay on infected Vero cell monolayers.

RP-FeLV:

An amino acid sequence for FeLV gp85 were used to generate codon-optimized (feline codon usage) nucleotide sequences in silico. Optimized sequences were prepared as synthetic DNA by a commercial vendor (ATUM, Newark, Calif.). Accordingly, a synthetic gene was designed based on the amino acid sequence of gp85. The construct (gp85_wt) was wild-type amino acid sequence [SEQ ID NO: 2], codon-optimized for feline, with flanking sequence appropriate for cloning into the alphavirus replicon plasmid.

The VEE replicon vectors designed to express FeLV gp85 were constructed as previously described [see, U.S. Pat. No. 9,441,247 B2; the contents of which are hereby incorporated herein by reference in their entireties], with the following modifications. The TC-83-derived replicon vector "pVEK" [disclosed and described in U.S. Pat. No. 9,441,247 B2] was digested with restriction enzymes Ascl and Pacl. A DNA plasmid containing the codon-optimized open reading frame nucleotide sequence of the FeLV gp85 genes, with 5' flanking sequence (5'-GGCGCGCCGCACC-3') [SEQ ID NO: 11] and 3' flanking sequence (5'-TTAATTAA-3'), was similarly digested with restriction enzymes Ascl and Pacl. The synthetic gene cassette was then ligated into the digested pVEK vector, and the resulting clone was re-named "pVHV-FeLV gp85". The "pVHV" vector nomenclature was chosen to refer to pVEK-derived replicon vectors containing transgene cassettes cloned via the Ascl and Pacl sites in the multiple cloning site of pVEK.

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference in their entireties]. Briefly, pVHV replicon vector DNA and helper DNA plasmids were linearized with NotI restriction enzyme prior to in vitro transcription using MegaScript T7 RNA polymerase and cap analog (Promega, Madison, Wis.). Importantly, the helper RNAs used in the production lack the VEE subgenomic promoter sequence, as previously described [Kamrud et al., *J Gen Virol.* 91(Pt 7):1723-1727

(2010)]. Purified RNA for the replicon and helper components were combined and mixed with a suspension of Vero cells, electroporated in 4 mm cuvettes, and returned to OptiPro® SFM cell culture media (Thermo Fisher, Waltham Mass.). Following overnight incubation, alphavirus RNA replicon particles were purified from the cells and media by passing the suspension through a ZetaPlus BioCap depth filter (3M, Maplewood, Minn.), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. Titer of functional RP was determined by immunofluorescence assay on infected Vero cell monolayers.

RP-RV

A vaccine was prepared comprising an alphavirus RNA replicon particle encoding the rabies virus glycoprotein (G) from rabies virus (RV) packaged with the capsid protein and glycoproteins of the avirulent TC-83 strain of Venezuelan Equine Encephalitis Virus. The nucleotide sequence for the rabies virus G protein was codon-optimized for humans. The resulting sequence has only ~85% nucleotide identity to a live rabies virus glycoprotein (G) sequence, despite having 100% amino acid identity. The vaccine can be used as a single dose administered to a mammalian subject, e.g., subcutaneously to cats and dogs aged 12 weeks or older or alternatively, in a multiple dose comprising a primary administration followed by one or more booster administrations.

An amino acid sequence for Rabies glycoprotein (G) was used to generate codon-optimized (human codon usage) nucleotide sequences in silico. Optimized sequences were prepared as synthetic DNA by a commercial vendor (ATUM, Newark, Calif.). Accordingly, a synthetic gene [SEQ ID NO: 9] was designed based on the amino acid sequence of Rabies Glycoprotein. The construct (RABV-G) was a wild-type amino acid sequence [SEQ ID NO: 10], codon-optimized for humans, with flanking sequence appropriate for cloning into the alphavirus replicon plasmid.

The VEE replicon vectors that were designed to express Rabies G were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes AscI and PacI. A DNA plasmid containing the codon-optimized open reading frame nucleotide sequence of the Rabies G gene, with 5' flanking sequence (5'-GGCGCGCCGCACC-3') [SEQ ID NO: 11] and 3' flanking sequence (5'-TTAATTAA-3') was similarly digested with restriction enzymes AscI and PacI. The synthetic gene cassette was then ligated into the digested pVEK vector, and the resulting clone was re-named "pVHV-RABV-G". The "pVHV" vector nomenclature was chosen to refer to pVEK-derived replicon vectors containing transgene cassettes cloned via the AscI and PacI sites in the multiple cloning site of pVEK.

Production of TC-83 RNA replicon particles (RP) was conducted according to methods previously described [U.S. Pat. No. 9,441,247 B2 and U.S. Pat. No. 8,460,913 B2; the contents of which are hereby incorporated herein by reference in their entireties]. Briefly, pVHV replicon vector DNA and helper DNA plasmids were linearized with NotI restriction enzyme prior to in vitro transcription using MegaScript T7 RNA polymerase and cap analog (Promega, Madison, Wis.). Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to OptiPro® SFM cell culture media (Thermo Fisher, Waltham, Mass.). Following overnight incubation, alphavirus RNA replicon particles were purified from the cells and media by passing the suspension through a ZetaPlus BioCap® depth filter (3M, Maplewood, Minn.), washing with phosphate buffered saline containing 5% sucrose (w/v), and finally eluting the retained RP with 400 mM NaCl buffer. Eluted RP were formulated to a final 5% sucrose (w/v), passed through a 0.22 micron membrane filter, and dispensed into aliquots for storage. Titer of functional RP was determined by immunofluorescence assay on infected Vero cell monolayers.

Example 2

Evaluation of the Safety of a Combination Vaccine Containing Two RP Constructs and Three Modified Live Fractions in Cats Various formulations and reconstitution methods of a lyophilized pentavalent feline combination vaccine were evaluated in regard to their safety in cats. The desired presentation of the pentavalent vaccine is a 0.5 mL dose, the optimal formulation and fill method is a 0.5 mL fill. The stabilizer contained 1.1% NZ-amine (a casein enzymatic hydrolysate), 1.1% gelatin, and 7.5% sucrose, with the percentages provided representing the final concentrations. Should the volume and final potency constraints for the addition of the five fractions necessitate a volume greater than 0.5 mL, the product can be formulated and filled to 1.0 mL and reconstituted with 0.5 mL of diluent. This doubles the concentration of stabilizer components in the administered dose. The safety of such a concentrated dose of stabilizer with these antigens had not previously been tested in cats.

A third option of a 1.0 mL fill volume rehydrated with 1.0 mL of diluent also was tested in the event that the 1.0 mL fill/0.5 mL rehydration format was not safe in cats. The vaccines were blended and then lyophilized. The vaccines contained an alphavirus RNA replicon particle that encodes a feline leukemia virus glycoprotein (RP-FeLV) and an alphavirus RNA replicon particle that encodes a feline calicivirus capsid protein (RP-FCV), together with the components of a commercially available vaccine, Nobivac® Feline-1, i.e., a modified live (MLV) feline panleukopenia virus (FPL), a modified live feline viral rhinotracheitis virus (FVR) and a modified live *Chlamydophila felis* in a stabilizer containing 1.1% gelatin, 1.1% NZ-amine and 7.5% sucrose. The various formulations of the pentavalent feline combination vaccine were prepared and reconstituted as described in the Table 1 below:

TABLE 1

FORMULATIONS OF THE PENTAVALENT COMBINATION VACCINE

| Treatment Group | No. of Cats | Test Product Antigens | Freeze-Dried Cake (Fill) Volume | Diluent (Rehydration) Volume |
|---|---|---|---|---|
| 1 | 6 | RP-FCV, RP-FeLV, | 1.0 mL | 1.0 mL |
| 2 | 6 | FPL, FVR & | 1.0 mL | 0.5 mL |

TABLE 1-continued

FORMULATIONS OF THE PENTAVALENT COMBINATION VACCINE

| Treatment Group | No. of Cats | Test Product Antigens | Freeze-Dried Cake (Fill) Volume | Diluent (Rehydration) Volume |
|---|---|---|---|---|
| 3 | 6 | *C. felis* | 0.5 mL | 0.5 mL |
| 4 | 2 | Diluent only | NA | 1.0 mL |

The vaccines were formulated to contain the same dose of each antigen (the 0.5 mL cake vaccine was formulated with twice the concentration of each antigen), the stabilizer was used at a constant concentration in all formulations (the 1.0 mL cake vaccine rehydrated with 0.5 mL diluent contained twice the concentration of stabilizer upon rehydration).

The experimental cat subjects were vaccinated with the indicated volume of the respective test vaccine at 7-8 weeks of age (typically having a minimum age of vaccination for the feline core vaccine) and again 21 days later. The cats were observed for a period of 15 minutes immediately after each vaccination for reactions to the test vaccine, which might indicate pain or discomfort, such as vocalization, stinging, itching, biting, sudden movement upon the injection of the vaccine, or any unusual reaction (see Tables 2 and 3 below). A clinical assessment was performed by a veterinarian 4 to 6 hours after the vaccination and each day for three days post-vaccination.

The clinical assessment included palpation of the injection site and observations for any local reactions including pain to touch, swelling, redness or abscess. Cats were also observed for any systemic reactions such as depression, lethargy, lameness, vomiting, tremors, agitation, and diarrhea. Body temperatures were also measured and recorded at 4 to 6 hours post-vaccination and each day for two days following each vaccination. Palpation of injection sites for local reactions was additionally performed three times each week between 7 days and 21 days after each vaccination.

All vaccine formulations and rehydration protocols were found to be safe. No local or systemic reactions were observed in any of the cats. Body temperatures at each measurement period for all cats were normal, with the exception of one cat in Treatment Group 3 (0.5 mL cake/0.5 mL diluent) which presented with a body temperature of 103.6° C. five hours post-second vaccination. Therefore, all three preparations of the pentavalent vaccine were found to be acceptable.

TABLE 2

IMMEDIATE REACTIONS TO VACCINATION WITH PENTAVALENT COMBINATION VACCINE

| Treatment Group | Vaccine ID | Vocalization | | Bite (during injection) | | Sudden movement away from injection | | Scratching at injection site (post-injection) | |
|---|---|---|---|---|---|---|---|---|---|
| | | 1st Vac. | 2nd Vac. | 1st Vac. | 2nd Vac. | 1st Vac. | 2nd Vac. | 1st Vac. | 2nd Vac. |
| 1 | Pentavalent Feline Vaccine 1.0 mL cake/1.0 mL diluent | 0/6 | 1/6 | 0/6 | 0/6 | 0/6 | 0/6 | 0/6 | 0/6 |
| 2 | Pentavalent Feline Vaccine 1.0 mL cake/0.5 mL diluent | 0/6 | 0/6 | 0/6 | 0/6 | 0/6 | 0/6 | 0/6 | 0/6 |
| 3 | Pentavalent Feline Vaccine 0.5 mL cake/0.5 mL diluent | 0/6 | 0/6 | 0/6 | 0/6 | 0/6 | 0/6 | 0/6 | 0/6 |
| 4 | Diluent only 1.0 mL | 1/2 | 1/2 | 0/2 | 0/2 | 1/2 | 1/2 | 0/2 | 0/2 |

TABLE 3

LOCAL/SYSTEMIC REACTIONS TO VACCINATION WITH PENTAVALENT COMBINATION VACCINE

| Treatment Group | Vaccine ID | Local Reactions (Redness, pain to touch, swelling or abscess) | | Systemic Reactions (vomiting, lameness, depression, lethargy, tremors, agitation or diarrhea) | | Body Temperature ≥ 103.5° C. Post-Vaccination | |
|---|---|---|---|---|---|---|---|
| | | 1st Vac. | 2nd Vac. | 1st Vac. | 2nd Vac. | 1st Vac. | 2nd Vac. |
| 1 | Pentavalent Feline Vaccine 1.0 mL cake/1.0 mL diluent | 0/6 | 0/6 | 0/6 | 0/6 | 0/6 | 0/6 |

TABLE 3-continued

LOCAL/SYSTEMIC REACTIONS TO VACCINATION WITH PENTAVALENT COMBINATION VACCINE

| Treatment Group | Vaccine ID | Local Reactions (Redness, pain to touch, swelling or abscess) 1$^{st}$ Vac. | 2$^{nd}$ Vac. | Systemic Reactions (vomiting, lameness, depression, lethargy, tremors, agitation or diarrhea) 1$^{st}$ Vac. | 2$^{nd}$ Vac. | Body Temperature ≥ 103.5° C. Post-Vaccination 1$^{st}$ Vac. | 2$^{nd}$ Vac. |
|---|---|---|---|---|---|---|---|
| 2 | Pentavalent Feline Vaccine 1.0 mL cake/0.5 mL diluent | 0/6 | 0/6 | 0/6 | 0/6 | 0/6 | 0/6 |
| 3 | Pentavalent Feline Vaccine 0.5 mL cake/0.5 mL diluent | 0/6 | 0/6 | 0/6 | 0/6 | 0/6 | 1/6 |
| 4 | Diluent only 1.0 mL | 0/2 | 0/2 | 0/2 | 0/2 | 0/2 | 0/2 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. An immunogenic composition comprising an alphavirus RNA replicon particle that encodes a feline calicivirus (FCV) capsid protein or an antigenic fragment thereof, and a modified live feline pathogen selected from the group consisting of a modified live feline viral rhinotracheitis virus (FVR), a modified live feline panleukopenia virus (FPLV), a modified live *Chlamydophila felis*, and any combination thereof.

2. The immunogenic composition of claim 1, wherein the capsid protein is selected from the group consisting of a FCV F9-Like capsid protein, an antigenic fragment of the FCV F9-Like capsid protein, a virulent systemic FCV (VS-FCV) capsid protein, an antigenic fragment of the VS-FCV capsid protein and any combination thereof.

3. The immunogenic composition of claim 2, wherein the capsid protein is a VS-FCV capsid protein or an antigenic fragment thereof.

4. The immunogenic composition of claim 3, that further comprises an additional alphavirus RNA replicon particle that encodes an FCV F9-Like capsid protein or an antigenic fragment thereof.

5. The immunogenic composition of claim 4, wherein the VS-FCV capsid protein comprises an amino acid sequence comprising at least 95% identity with the amino acid sequence of SEQ ID NO: 2.

6. The immunogenic composition of claim 5, wherein the FCV F9-Like capsid protein comprises an amino acid sequence comprising at least 95% identity with the amino acid sequence of SEQ ID NO: 4.

7. The immunogenic composition of claim 2, wherein the capsid protein is a FCV F9-Like capsid protein or an antigenic fragment thereof.

8. The immunogenic composition of claim 2, that comprises one or more additional alphavirus RNA replicon particles that encode an antigen selected from the group consisting of an FeLV glycoprotein (gp85), an antigenic fragment of the gp85, a rabies virus G protein, an antigenic fragment of the rabies virus G protein, and any combination thereof.

9. The immunogenic composition of claim 8, wherein the FeLV glycoprotein (gp85) comprises an amino acid sequence comprising at least 95% identity with the amino acid sequence of SEQ ID NO: 6.

10. The immunogenic composition of claim 8, wherein the additional alphavirus RNA replicon particle is a Venezuelan Equine Encephalitis (VEE) alphavirus RNA replicon particle.

11. A vaccine to aid in the prevention of disease due to FCV comprising the immunogenic composition of claim 8, and a pharmaceutically acceptable carrier.

12. The immunogenic composition of claim 2, wherein the alphavirus RNA replicon particle is a Venezuelan Equine Encephalitis (VEE) alphavirus RNA replicon particle.

13. The immunogenic composition of claim 3, wherein the alphavirus RNA replicon particle also encodes an antigen selected from the group consisting of an FCV F9-Like capsid protein, an antigenic fragment of the FCV F9-Like capsid protein, a feline leukemia virus (FeLV) glycoprotein (gp85), an antigenic fragment of the gp85, a rabies virus G protein, an antigenic fragment of the rabies virus G protein, and any combination thereof.

14. The immunogenic composition of claim 13, wherein the rabies virus G protein comprises an amino acid sequence comprising at least 95% identity with the amino acid sequence of SEQ ID NO: 10.

15. A vaccine to aid in the prevention of disease due to FCV comprising a Venezuelan Equine Encephalitis (VEE) alphavirus RNA replicon particle that encodes a virulent systemic feline calicivirus (VS-FCV) capsid protein or an antigenic fragment thereof, a modified live feline viral rhinotracheitis virus (FVR), a modified live feline panleukopenia virus (FPLV), and a modified live *Chlamydophila felis*, and a pharmaceutically acceptable carrier.

16. The vaccine of claim 15, further comprising a Venezuelan Equine Encephalitis (VEE) alphavirus RNA replicon particle that encodes a feline calicivirus F9-Like capsid protein or an antigenic fragment thereof.

17. The vaccine of claim 15, wherein the VEE alphavirus RNA replicon particle further encodes a feline calicivirus F9-Like capsid protein or an antigenic fragment thereof.

18. The vaccine of claim 17, further comprising a Venezuelan Equine Encephalitis (VEE) alphavirus RNA replicon particle that encodes feline leukemia virus (FeLV) glycoprotein (gp85) or an antigenic fragment thereof.

19. The vaccine composition of claim 18, that is a nonadjuvanted vaccine.

20. A method of immunizing a feline against a pathogenic FCV comprising administering to the feline an immunologically effective amount of the vaccine of claim 19.

* * * * *